United States Patent
Soderstrom

(10) Patent No.: US 7,456,399 B1
(45) Date of Patent: Nov. 25, 2008

(54) CALIBRATING MULTIPLE PHOTOELECTRON SPECTROSCOPY SYSTEMS

(75) Inventor: Eric J. Soderstrom, Palo Alto, CA (US)

(73) Assignee: ReVera Incorporated, Sunnyvale, CA (US)

( * ) Notice: Subject to any disclaimer, the term of this patent is extended or adjusted under 35 U.S.C. 154(b) by 381 days.

(21) Appl. No.: 11/395,189

(22) Filed: Mar. 30, 2006

(51) Int. Cl.
*H01J 40/00* (2006.01)
*H01J 47/00* (2006.01)

(52) U.S. Cl. .................. 250/305; 250/306; 250/307; 702/28; 702/27; 702/189; 702/182; 378/50; 378/88; 378/89; 378/90; 356/302; 438/50

(58) Field of Classification Search ......... 250/305–307; 435/50; 378/50, 88–90; 702/27, 28, 189, 702/182; 356/302
See application file for complete search history.

(56) References Cited

U.S. PATENT DOCUMENTS 6,800,852 B2 * 10/2004 Larson et al. ............... 250/305
6,891,158 B2 * 5/2005 Larson et al. ............... 250/305

* cited by examiner

*Primary Examiner*—Jack I. Berman
*Assistant Examiner*—Meenakshi Sahu
(74) *Attorney, Agent, or Firm*—Blakely, Sokoloff, Taylor & Zafman LLP

(57) ABSTRACT

A method comprising obtaining a first set of spectral data for a first sample film measured by a first system, extracting intensities for one or more elemental species associated with the first sample film to provide a first set of extracted intensities using a function, and determining a first quantitative characteristic associated with the first sample film using the first set of extracted intensities. Next, obtain a second set of spectral data measured for a comparable sample film measured by a second photoelectron spectroscopy system. Next, apply the same function and continually adjust the function to extract intensities for the respective elemental species associated with the comparable sample film to provide a second set of corrected-extracted intensities. A second quantitative characteristic for the comparable sample is determined. The function is continually adjusted until the determined second quantitative characteristic closely or substantially matches the first quantitative characteristic.

29 Claims, 11 Drawing Sheets

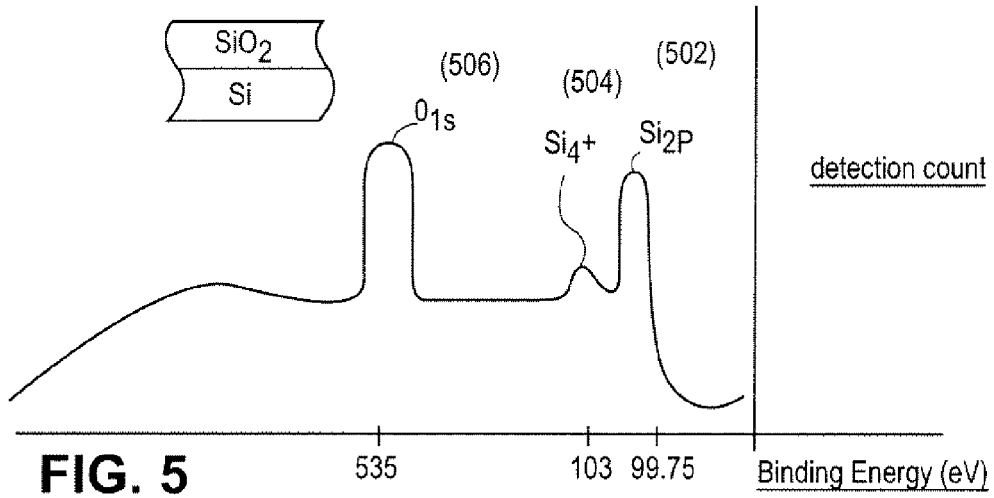

FIG. 5

$I_1 - I_{2-c} *$ Transmission Correction $= 0$ $I_{Si_4+}$(system 1) $-$ $I_{Si_4+}$(system 2) $*$ Transmission Correction $(Si_4+) = 0$ e.g., $\quad 47.5 \quad - \quad 50 \quad * \quad \dfrac{T_{(103)}}{T_{(103)}} = 0$
$\quad\quad\quad\quad\quad\quad\quad\quad\quad\quad\quad\quad\quad\quad\quad = 0.95$ $I_{O_{1s}+}$(system 1) $-$ $I_{O_{1s}+}$(system 2) $*$ Transmission Correction $(O_{1s}) = 0$ e.g., $\quad 200 \quad - \quad 190 \quad * \quad \dfrac{T_{(535)}}{T_{(535)}} = 0$
$\quad\quad\quad\quad\quad\quad\quad\quad\quad\quad\quad\quad\quad\quad\quad = 1.05$

FIG. 6

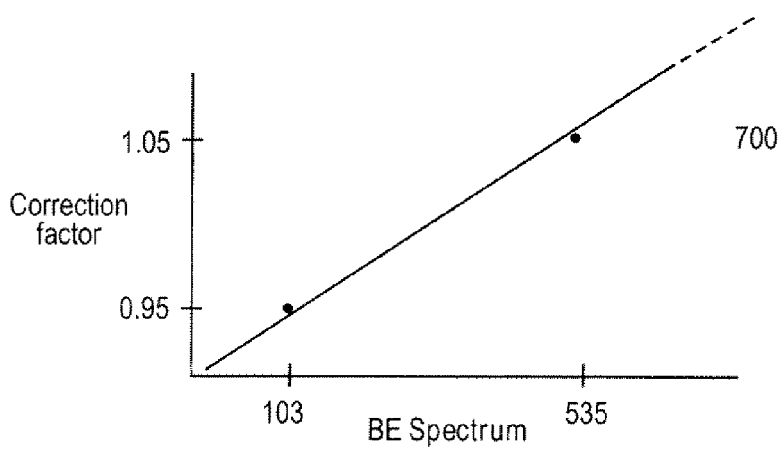

FIG. 7

CALIBRATING MULTIPLE PHOTOELECTRON SPECTROSCOPY SYSTEMS

FIELD

Embodiments of the present invention relate to the characterization of films. More particularly, the present invention pertains to a method and apparatus that characterize a film with a capability of matching spectral data among multiple systems.

BACKGROUND

Characterization or analysis of samples (e.g., thickness of a thin film, elemental and/or chemical species concentration in a thin film formed on a substrate, etc.) is necessary in the manufacture of many different types of devices (e.g., electronic and optical electronic devices). For example, it may be necessary to determine the composition of thin dielectric films (e.g., gate oxide films, tantalum nitride films, etc.) formed in known semiconductor integrated circuit devices, such as processing devices and memory devices. Increases in the density of such devices on an integrated circuit chip and reduction in device dimensions require the advancement of production processes and characterization technologies related to the materials used to fabricate such devices.

Various techniques have been used for characterization of films, e.g., to provide thickness measurements and/or to determine the concentration of trace and/or major components in such films. For example, several of such methods include ellipsometry, transmission electron microscopy (TEM), scanning transmission electron microscopy (STEM), secondary ion mass spectrometry (SIMS), x-ray photoelectron spectrometry (XPS) (also known as electron spectroscopy for chemical analysis (ESCA)), Auger electron spectrometry (AES), and other electron beam methods.

XPS, or ESCA, has been previously used to characterize thin films (e.g., ultra thin films less than 5 nanometers) such as lubricant coatings on computer hard disks with a measurement precision of 5% RSD (Relative Standard Deviation). Further, characterization of other types of films such as SiON via XPS using standard practices has resulted in measurement precisions of 0.5% to 1.0% RSD.

From any of the mentioned technique, spectral data for a sample film are obtained. Spectral peaks are also obtained for different components in the sample film. Spectral peaks are generally, electron energy counts for detected electrons irradiated from the sample film. Some means of extracting intensities are then applied to extract intensities representatives of the peaks. Such means for intensity extraction include algorithm or mathematical functions that perform basis function determination, slope analysis, peaks area calculation, Gaussian, Lorentzian, or predetermined Basis functions that can be applied to fit a spectral peak to a shape and extract an intensity value representative of such spectral peak. The extracted intensities are then used in determining the characteristic of the sample film such as film thickness, component dose and component concentration in the film.

Currently, when a spectroscopy system such as XPS is used, there has to be calibration or matching procedures for the hardware elements for all necessary systems so that the results obtained on the systems are in agreement among one another. Typically, the manufacturers perform the calibration procedures of the system. Such calibration procedures have to be done in a way that gives as close to similar physical behavior as possible among all systems. Even with the calibration done, a linear gain and/or offset correction may still need to be applied to the results on multiple systems to be used so as to get similar responses among all systems.

Under the current practice, characteristic values determination on multiple systems or tools (e.g., multiple XPS systems) require linear gain and offset correction between all systems so that the results from one system can match the results from another system.

In a simple illustration, a first film is analyzed under tools 1 and 2. The results obtained from tool 1 may yield, for example, a thickness value of 5.6 Angstroms and from tool 2, a thickness value of 6.0 Angstroms. A second film analyzed under tools 1 and 2 may yield a thickness value of 11.0 Angstrom on tool 2 and 12.1 Angstrom on tool 1. A correlation is determined for both tools (FIG. 1). A best-fit line is applied to the correlation. An offset and slope values are determined for the best-fit line. In this example, Tool 1=Offset+Slope (Tool 2)
Slope=1.1
Offset=−1

The slope and offset values constitute the matching error for the tools 1 and 2. Thus, under the current practice, each characteristic determination must be done prior to the determination of the matching error between the two tools or systems.

Designing and calibrating hardware elements on multiple systems (e.g., XPS systems) need to give as close to similar physical behavior as possible between the systems. A final step of applying a linear gain and offset correction to each measurement has shown to be unmanageable for broad array of possible film compositions and time consuming.

SUMMARY

Embodiments of the present invention pertain to apparatuses and methods for characterizing samples with a capability of matching data among multiple systems so that the results obtained from the multiple systems are in agreement.

Embodiments of the present invention pertain to a method, system, and apparatus that calibrate two or more systems to each other by correcting the spectroscopic intensities extracted from the spectral data obtained from the systems. One system will act as a control system while other systems will calibrate to the control system by having their data matched to those obtained from the control system. The spectral data obtained from a system to be matched (system 2) is fitted to an adjusted function so that the extracted intensity data from the system 2 match the extracted intensity data for the control system (system 1). In this discussion, system 1 is often indicated to be a control system. It is to be understood that another system, system 2, 3, or 4 may very well be the control system and the discussion would similarly apply. It is the corrected intensity data extracted from the spectral data using the adjusted function that can be used for various characteristic determinations for a film. Using this method, characteristic determination results obtained from one system would match another system.

In one embodiment, the data from system 1 and the data from system 2 are minimized to one another by using an adjusted function. For instance, the shape of the fits, the basis functions, or other functions used to extract the intensities of the spectral peaks are adjusted until the characteristic measurements determined using the intensities (e.g., thickness) are in agreement. In other words, intensities extracted for the elements in the film are obtained by having the shape function or fit (e.g., basis function) used to extract such intensities from the raw spectral data adjusted. Thus, intensities extracted from system 2 would closely match the intensities extracted from system 1. The extracted intensities are then used for film characteristic determination. The characteristic measurements obtained from system 2 thus match the measurements obtained from system 1 for a particular film and a particular characteristic measurement.

A method for use in characterizing a film according to the present invention includes providing an acquired spectrum for a film to be characterized (e.g., a dielectric film such as a silicon oxynitride film and/or a film having a thickness of less than about 10 nanometers, and even less than about 4 nanometers), wherein the film is formed on a substrate (e.g., silicon containing material). The acquired spectrum includes a spectral peak shape representative of at least one component (or elemental species) in the film and at least an additional spectral peak shape representative of a component in the substrate. A particular function (e.g., a chosen basis function) is used to extract intensities for one or more elemental species associated with the sample film to provide a first set of extracted intensities. A first quantitative characteristic associated with the first sample film is determined using the first set of extracted intensities. A second set of spectral data associated with a comparable sample film measured by a second photoelectron spectroscopy system is obtained. The comparable sample film can be the same sample as the first sample film or another film that can be characteristically compared to the first sample film. The same function used for the first set of extracted intensities extraction is used and applied to the second set of spectral data to extract intensities. On the second set of data, the function is continually adjusted to extract intensities for the elemental species associated with the comparable sample film to provide a second set of corrected-extracted intensities. The second set of corrected-extracted intensities is so termed because an adjusted function is used to extract the intensities. A second quantitative characteristic for the comparable sample film is determined using the second set of corrected-extracted intensities. The function is continually adjusted until the determined second quantitative characteristic closely or substantially matches the first quantitative characteristic. For example, when the first set of intensities is used to determine a film thickness for the sample film, the second set of intensities is extracted with the adjusted function such that when the second set of corrected-extracted intensities is used to determine the same film thickness, the results will be the same.

In one embodiment, a transmission correction factor is determined for each intensity value of the second set of corrected-extracted intensities. A transmission correction factor is a value that brings a corrected-extracted intensity to be equal to a respective intensity from the first set of extracted intensities. An adjusted function is also determined based on the adjusting step described above. The adjusted function and the transmission correction factor can be applied to the data obtained for subsequent measurements on the second system during the intensity extraction step.

In one embodiment, a system for characterizing a film while matching results from the system to a control system is provided. The system comprises an x-ray source operable to irradiate one or more films with x-rays resulting in an escape of photoelectrons, an analyzer operable to detect escaping photoelectrons wherein the analyzer is operable to generate a signal representative of detected photoelectrons for use in providing an acquired spectrum for the film, and a computer apparatus operable to take spectral data, extract spectral intensities and adjust the spectral data. The computer apparatus is able to recognize a spectral peak shape of the acquired spectrum of at least one component of the film, wherein the film is formed on a substrate. The computer apparatus is also able extract one or more intensity values associated with the acquired spectrum using a selected shape function for each spectral peak. The computer apparatus is able to continually adjust selected shape functions to extract appropriate intensity values. The selected shape function is adjusted until the extracted intensity value is in agreement with a control intensity value extracted from a respective control spectrum using the same selected shape function measured from a control system. The computer apparatus is also able to store an adjusted shape function for the intensity value. The adjusted shape function is obtained when the extracted intensity value is in agreement with the control intensity value.

Likewise, the computer apparatus is also able to continually adjust transmission correction factors to extract appropriate intensity values. The selected transmission correction factor is adjusted until the extracted intensity value is in agreement with a control intensity value extracted from a respective control spectrum using a transmission factor measured from a control system. The computer apparatus is also able to store a transmission correction factor for the intensity value. The transmission correction factor is obtained when the extracted intensity value is in agreement with the control intensity value. The computer apparatus is also able to continually adjust selected shape functions and transmission correction factors simultaneously to extract appropriate intensity values. This simultaneous adjustment capability allows for the best possible agreement with the control intensity value. The computer apparatus is also able to determine at least one quantitative measurement for the film using the extracted intensities. In this process, the computer is able to retrieve the stored adjusted shape functions and transmission correction factors and apply them in calculating the intensities used in determining the quantitative measurement, thus insuring its agreement with the same quantitative measurement on the control system.

In one embodiment the quantitative measurements of interest all involve intensity ratios, such as calculating the film thickness, the dose level of a particular element, or the atomic concentrations of all elements present in the film. In this case the transmission correction factor need only be determined so as to represent the relative transmission difference as a function of peak energy, or equivalently the element binding energy, of system 2 with respect to system 1. This allows systems with large differences in absolute peak intensity to have such measurements calibrated into agreement without the overall intensity level difference being determined. As well, the relative transmission difference does not change as the intensity of the X-Ray source degrades with time making the calibration in this case valid for the lifetime of the X-Ray source.

In one embodiment, a program storage media, readable by a media read apparatus under control of a computer, tangibly embodying a program executable to perform a process for characterizing a film while matching results from the system to a control system is used.

BRIEF DESCRIPTION OF THE DRAWINGS

The embodiments of the present invention are illustrated by way of example and not by way of limitation in the figures of the accompanying drawings in which like references indicate similar elements. The invention may best be understood by referring to the following description and accompanying drawings that are used to illustrate embodiments of the invention. It should be noted that references to "an" or "one"

embodiment of the invention in this disclosure are not necessarily to the same embodiment, and they mean at least one. In the drawings:

FIGS. 5-7 illustrates an exemplary method of calibrating multiple systems to one another according to the present invention using several elemental species and a capability for interpolation and extrapolation;

DETAILED DESCRIPTION

Figure 1:
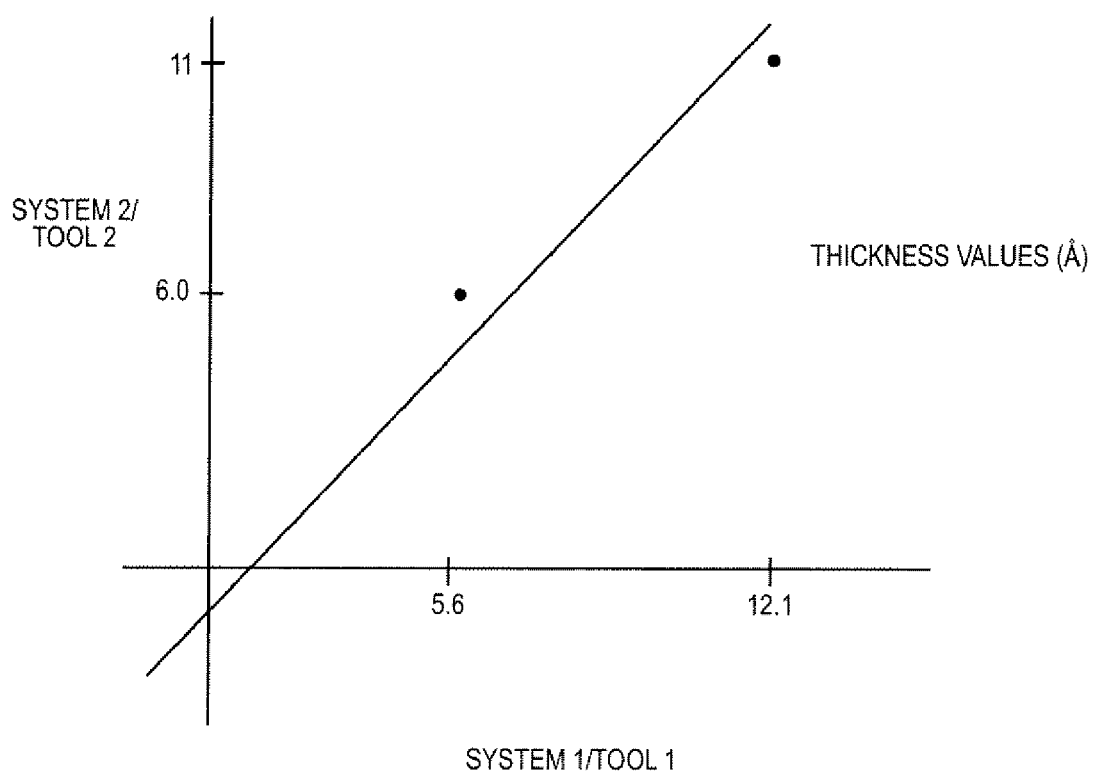
FIG. 1 illustrates an example of linear correlation between measurements obtained on two different systems/tools.

Exemplary embodiments are described with reference to specific configurations and techniques. Those of ordinary skill in the art will appreciate the various changes and modifications to be made while remaining within the scope of the appended claims. Additionally, well known process steps, calculations, and the like are not set forth in detail. For example, method for background subtraction in a spectrum is not discussed herein although it may be used in obtaining each spectrum for a film.

The immediately following sections describe an example of an analysis system (e.g., XPS) that will benefit from embodiments of the present invention. Embodiments of the present invention pertain to a method, system, and apparatus that characterize films while calibrating two or more systems (such as two or more XPS systems) to each other by correcting the spectroscopic intensities extracted from the spectral data obtained from the systems. One system will act as a control system while other systems will calibrate (or match) to the control system by having their data adjusted to match to those obtained from the control system. Thus, from the control system, spectral data for a film is obtained. A selected function (e.g., basis function) is then applied to the spectral date in order to extract intensity values for the peaks in the spectral data (control intensity values). From the system to be matched to the control system, spectral data (second spectral data) for a comparable, identical, or similar film are obtained. The same selected function is applied to the second spectral data except that the selected function is an adjusted so that the extracted intensity values from the second spectral data match the control intensity values. Film characteristic determinations using the extracted intensity values would be in agreement among all systems including the control system. Again, it is to be noted that system 1 is often indicated to be a control system. It is to be understood that another system, system 2, 3, or 4 may very well be the control system and the discussion would similarly apply.

To obtain a spectral data for a film, an analysis system such as an XPS system is used. The film, typically formed on a substrate, is placed into the system and the energy values for detectable photoelectrons are measured and analyzed. Before discussing in details the methods of matching values obtained on multiple systems, an analysis system that can be used for the embodiments of the present invention is described.

Exemplary methods, systems and apparatus of the present invention may be used to analyze complex materials in development processes, assist to identify solutions for processing problems, identify contamination sources, improve yields in the fabrication of devices, assist in monitoring processing and manufacturing devices, and be used in failure analysis techniques. Further, the methods, systems and apparatus may be used in the characterization of thin films relating to various industrial applications, such as semiconductor devices, magnetic storage media, display technology, automotive materials, aerospace materials, polymer products, and/or biomaterials.

Generally, the methods, systems and apparatus described herein preferably provide non-destructive, e.g., non-invasive, analysis systems and methods that generally include the collection of surface spectral measurements (e.g., XPS spectra) from a thin film. The intensities representatives of the spectra are extracted and adjusted through minimization techniques to a control system's values. Thereafter, a characteristic of the thin film formed by a particular process defined by a set of processing conditions, e.g., thickness of a thin nitrided silicon oxide film, nitrogen concentration in the thin nitrided silicon oxide film, etc., can be determined based on the intensities. Embodiments of the present invention also provide a method and system for adjusting extracted intensities obtained from multiple systems to a selected control system so that results from one system would match results from another system.

Generally, for example, with regard to silicon dioxide or nitrided oxide films, it is to be appreciated that films of different components can similarly be analyzed using embodiments of the present invention. A film can be formed on a substrate. In one embodiment, a silicon oxynitride film (which as used herein represents any film formed of silicon, oxygen, and nitrogen) is formed on a silicon substrate. In one embodiment, the present invention performs surface spectral measurements to provide the Si2p region (i.e., $Si_{2p}$/Si4+) of the XPS spectra of the film. Methods of the present invention enable various characteristic determinations for the film; for example, the thickness of the silicon oxynitride gate film can be calculated using the Si2p spectrum. Further, the concentration of film components, e.g., nitrogen in the silicon oxynitride film can be calculated using the Si2p and nitrogen N1s spectra. In addition, for example, film uniformity may be determined by repeating the thickness and/or dose measurements at multiple locations on a wafer on which the silicon oxynitride film is deposited. Similarly, in other embodiments, an $SiO_2$ film is used for characterization and system matching. In those embodiments, spectral data from species represented by the binding states $O_{1s}$, $Si_{4+}$, and $N_{1s}$ are obtained and used for the analysis.

Figure 2:
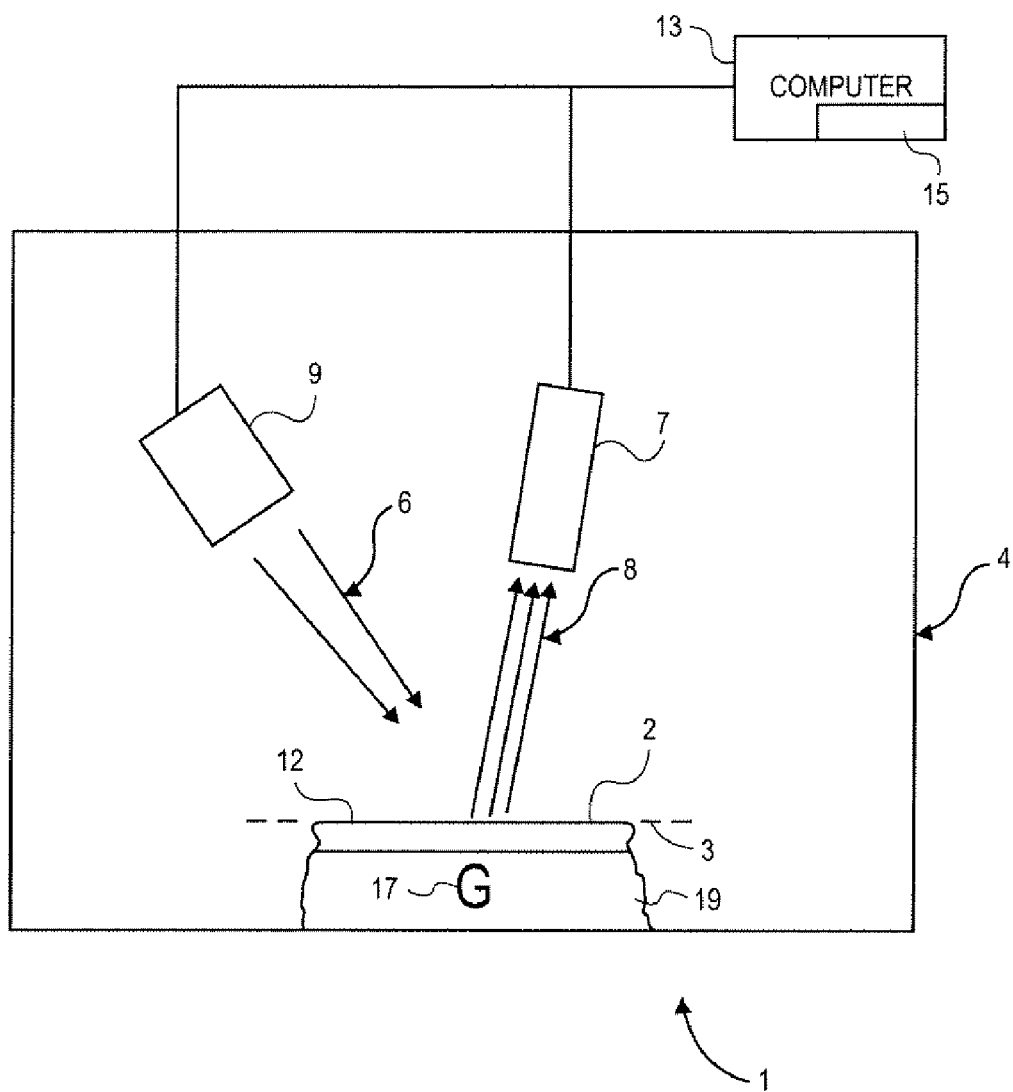
FIG. 2 illustrates an exemplary embodiment of an analysis system (e.g., XPS system) that can characterizes a film with a capability of matching spectral intensities among multiple systems.

FIG. 2 generally shows one embodiment of an illustrative analysis system 1 operable for use in characterizing a film 2 having a sample surface 12 positioned at an analysis plane 3 of an analysis instrument 4; the film 2 having been formed on a substrate 19. Coupled to the analysis instrument 4 is a computer apparatus 13 operable under control of one or more programs 15 to carry out one or more various characterization processes, e.g., film thickness. The computer apparatus 13 is also operable under one or more programs to carry out the minimization processes for the system 1 to a control system (much like the system 1).

The film 2 having the film surface 12 may be formed of any one or more components. The term component is defined herein as one or more elements and/or chemical species. For example, such components may include elements and/or chemical species composing materials used in semiconductor fabrication, magnetic storage media, or any of the other various applications described above. In other words, for example, in the context of semiconductor fabrication the film may include layers formed of oxygen, silicon, carbon, fluorine, silicon dioxide, nitrogen, etc.

Preferably, the present invention is useful in the characterization of thin films, particularly thin dielectric or insulating films. As used herein, a thin film refers to a film or layer having a thickness of less than about 10 nanometers. However, the present invention may be beneficial in characterizing films as thick as 100 nanometers and is particularly beneficial for analyzing films having a thickness of less than 4 nanometers.

Further, the present invention is particularly advantageous in characterization of certain oxide layers. For example, such oxide layers may include silicon oxide layers, silicon oxynitride films, nitrided oxide layers, etc. For example, such oxide layers may be formed as thin films having thicknesses less than about 10 nanometers, and even less than 4 nanometers, and used for gate oxides in the fabrication of semiconductor devices such as field effect transistors (FET). Such transistors are used in various integrated circuit devices including processing devices, memory devices, etc. More particularly, the present invention is particularly advantageous in matching multiple systems to a control system in that there is no need to correct individual results as currently being done, but rather, the functions used to extract the intensities from the spectral data are adjusted so that the intensities used for various characteristic determination can be in agreement among multiple systems.

Certain embodiments of the present invention utilize the characterization of, for example, silicon oxide and silicon oxynitride films. It is to be appreciated that embodiments of the present invention may also be useful for characterizing other thin dielectric films, such as those with dopants other than nitrogen. For example, the present invention may be useful in characterizing thin dielectric films such as transition metal oxides and tantalum nitride. In other words, one skilled in the art will recognize that the present invention is not limited to any particular thin film, such as silicon oxynitride, but may be effective for characterizing other thin films as well.

Further, in various embodiments herein, silicon oxynitride is characterized using the present invention. However, in many instances, a starting film (i.e., a precursor film) of silicon oxide is used and then later nitrided to form a silicon oxynitride film. The present invention may be effective to measure the precursor silicon oxide film thickness as well as the later grown silicon oxynitride film. This may be particularly beneficial in process control since the final silicon oxynitride film thickness is partially dependent on the precursor silicon dioxide film thickness.

As one skilled in the art will recognize from the description above, the film may take one of many different forms. For example, the film may be a layer formed on a substrate or a region formed within a substrate, as well as any other film or stack of layers formed of a material that would benefit from being characterized according to the present invention. In other words, the term film as used herein refers to both a single film and films formed of multiple layers (e.g., a stack of layers).

Further, the term substrate as used herein is representative of almost any object upon which material may be formed or in which material may be formed, and the present invention is not to be taken as limited to any particular material or structure listed herein. However, the present invention does have particular advantages in characterizing certain thin films, e.g., gate dielectric layers such as gate oxide layers, formed on a silicon substrate.

As used herein, characterization refers to the determination of one or more characteristics of the film being analyzed. For example, characterization may refer to the determination of concentration of components in a film, the distribution of such components, or the determination of one or more other physical or chemical characteristics of the film, e.g., thickness, bonding states, elemental and chemical composition in the regions, etc. The present invention is particularly beneficial in the determination of thickness and concentration of components (e.g., elements and/or chemical species) in thin films.

Preferably, computer apparatus 13 includes a computing system operable to execute software 15 to provide for the characterization of films according to the present invention. Although the computer apparatus 13 may be implemented using software 15, executable using a processor apparatus, other specialized hardware may also be used to provide certain functionality required to provide a user with characterization of a film. As such, the term computer apparatus 13 as described herein includes any specialized hardware in addition to processor apparatus capable of executing various software routines.

The computer apparatus 13 may be, for example, any fixed or mobile computer system, e.g., a personal computer, and/or any other specialized computing unit provided as a functional part of or as a supplement to an analysis instrument used according to the present invention. The exact configuration of the computer system is not limiting, and most any device capable of providing suitable computing capabilities and/or control capabilities may be used according to the present invention. Further, various peripheral devices, such as a computer display, a mouse, a keyboard, a printer, etc., are contemplated to be used in combination with a processor in the computer apparatus 13. For example, a computer display or printer may be used to print or display various types of information, e.g., peak shapes and areas showing concentration of components (e.g., elements and/or chemical species) of the film, distributions of components of a film across a wafer on which it is formed, spectra of the components, etc.

In one embodiment, the computer apparatus 13 includes a program (included with the software 15 or in addition to the software 15) that carries out the method of matching a control system, e.g., the system 1, to another system as will be described below.

The analysis instrument 4 of the analysis system 1 may be any instrument that provides spectral data that can be analyzed using the data processing techniques described herein. Preferably, according to the present invention, the analysis instrument 4 of the analysis system 1 includes an x-ray source 9 operable to irradiate the film 2 with x-rays 6 resulting in the escape of photoelectrons from an analysis volume including a portion of the film 2 and a substrate portion therebelow. The x-rays 6 penetrate deep into the film surface 12, exciting photoelectrons 8 to escape from the film 2 and also, most likely, from at least a region of the substrate 19 upon which the film 2 is formed depending on the thickness of the film 2. However, photoelectrons can travel only a short distance before their energy is modified due to interaction with neighboring atoms. Only photoelectrons that escape at their original energy contribute to a peak in a spectrum used for the analysis of the film. Depending on the escape depth of the constituents of the sample volume, the average depth of analysis for a surface irradiated by x-rays 6 is in the range of about 10 angstroms to about 150 angstroms depending upon the sample material. The photoelectron energies generally include a high energy peaks in the range of 10-100 eV below the energy of the incident X-Rays from low binding energy states of Silicon, Aluminum, Halfnium or Oxygen present in the film, intermediate binding energy peaks, for example from the 1 s electrons of Nitrogen at 400 eV below the incident X-Ray energy, as well as higher binding energy peaks or lines characteristic of elemental and/or chemical species in the irradiated analysis volume extending all the way up to the incident X-Ray energy.

An analyzer 7 of the analysis system 1 is operable to detect photoelectrons 8 escaping from, for example, the film 2 and underlying substrate. The analyzer 7 is positioned at an analyzer angle (as further described below) relative to the analysis plane 3 or, in other words, relative to the film surface 12 which is preferably in the analysis plane. The analyzer 7 is used to detect photoelectrons for generation of a signal representative thereof to be used for the characterization of the film 2. Signals from the analyzer corresponding to intensity of detected photoelectrons are provided to the computer apparatus which operates on the signals to provide photoelectron energy information and thereby surface spectra measurements of components that are present in the analyzed volume, e.g., the film irradiated and a portion of the underlying substrate.

The analysis system 1 diagrammatically shown in FIG. 2 is operable to perform surface spectra measurements for use in the characterization processes described herein. When the system 1 needs to be matched to a control system, adjustment to the basis functions or other appropriate functions used to extract the intensities form the spectral measurements are adjusted to match those obtained from the control system. An adjustment to the function used to extract a peak intensity is performed so that the extracted peak intensity closely matches or minimizes to a respective extracted peak intensity form a control system. A transmission correction factor is also determined to equate the intensities from the system to the control system. A transmission correction factor can be understood to be a number that will make the extracted and corrected intensity to be equal to the respective intensity from the control system. For computation of quantitative characteristics which involve only ratios of intensities the determination of the shape of the transmission correction factor as a function of electron energy relative to the control system is sufficient. Upon the collection of surface spectra measurements and necessary adjustment to the spectral data, film characterization may be performed using the intensities. Film characterization methods may include thickness measurements for the film, dose concentration calculations, etc.

The system 1 illustrated above may be a conventional XPS system (e.g., those distributed under the trade designations PHI 5800, PHI Quantum 2000 Scanning ESCA Microprobe™ and PHI Quantera Scanning XPS Microprobe™ available from Physical Electronics, Inc. (Eden Prairie, Minn.)). The systems may be modified and/or operated at one or more of the parameters described herein to provide for thin film analysis. Embodiments of the present invention pertain to matching measurements among systems (or calibration) so that a film or films can be characterized on different systems and be expected to yield the same results among the systems.

Figure 3:
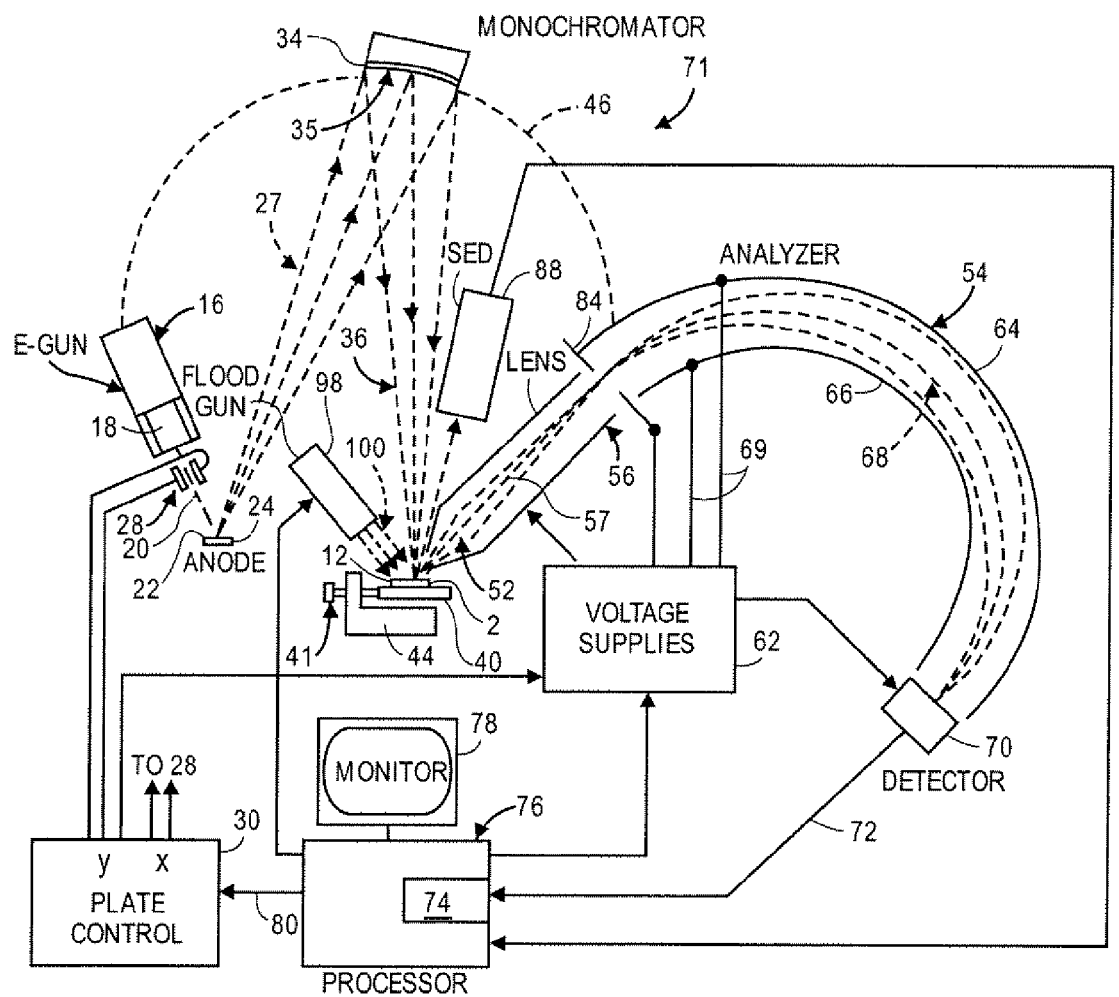
FIG. 3 illustrates an exemplary embodiment of an analysis system (e.g., XPS system) in more details that can characterizes a film with a capability of matching spectral intensities among multiple systems.

FIG. 3 shows in more detail one illustrative embodiment of portions of an analysis system 1 operable for carrying out the characterization according to the present invention. FIG. 3 was previously described in U.S. Pat. No. 5,315,113 to Larson et al., issued 24 May 1994, and entitled "Scanning and High Resolution X-ray Photoelectron Spectroscopy and Imaging," which is hereby incorporated by reference in its entirety. The detailed diagram of FIG. 3 is but one illustrative embodiment of an x-ray source and an analyzer that may be used according to the present invention and is not to be construed as limiting the present invention to any particular components shown therein.

The instrument 71 of FIG. 3 includes an electron gun 16 having an appropriate electron lens system 18 for focusing the electron beam 20 onto the surface 22 of a target anode 24. The electron gun 16 may be a conventional type, modified to optimize for higher power and larger beam size. The gun beam 20 is focused to a selected spot on the anode surface 22. The spot is preferably as small as practical, e.g., down to about 4 microns. The focusing of the beam 20 onto the spot of the anode surface results in the generation of x-rays 27 from the anode 24 and, in particular, from the selected anode spot. The electron gun may be any suitable gun such as one operable at 20 kV over 1 watt to 60 watts with a selectable beam size of 4 microns to 200 microns, such as described in U.S. Pat. No. 5,315,113.

The target anode 24 may be formed of any metal such as aluminum that provides a desired x-ray emission energy band. For example, the band is generally substantially a line of small energy width. Preferably, the target anode is at or near ground potential, and the gun cathode is operated at a negative voltage, for example, −20 kV, with respect to the anode to effect generation of x-rays including the desired band of x-rays of predetermined energy. In one preferred embodiment, the selected energy band is the aluminum K-alpha line at 1.4866 keV.

Although a monochromatic Al Kα x-ray source is used in the above exemplary embodiment of analysis instrument 71, it may be advantageous from a cost and measurement speed perspective to use other x-ray sources. For example, a non-monochromatic x-ray source such as Mg or Al Kα x-ray sources may provide additional speed in collecting surface spectra measurements.

Deflection plates 28 selectively direct or aim the electron beam 20 from the electron gun 16 to the spot on the anode 24 which is selected out of an array of such spots on the anode surface 22. Voltages from a deflection plate control 30, controlled by a processor 76 via line 80, are applied to the deflector plates, which are arranged in both x and y axes, to establish the amount of deflection of the beam, and thereby the selected position of the spot. The spot may be held stationary. Alternatively, the control 30 may provide rastering of the focused electron beam 20 across the flat surface of the anode, e.g., over the array of anode spots across the anode surface, and the x-rays 27 are emitted sequentially from successive anode spots. For example, raster speed may be 100 Hz in the dispersive direction and 10 kHz in the non-dispersive direction.

A Bragg crystal monochromator 34, advantageously single-crystal quartz, is disposed to receive a portion of the x-rays 27 from the anode 24. The monochromator has a crystallographic orientation and a concave configuration 35 to select and focus a beam of x-rays 36 in the desired energy band, e.g., the K-alpha line, as an x-ray spot on the film surface 12 to be analyzed. The x-ray spot is an image of the anode spot on the film surface 12. Alternatively, rastering of the x-ray spot may be used to cover a desired area of the sample surface. The film 2 rests on a stage 40 advantageously having orthogonal micrometer positioners 41 for manual or motorized positioning with respect to a support 44 in the instrument. The film 2 may be moved to provide coverage over an even larger surface area.

Although a Bragg crystal monochromator is preferred, other focusing apparatus may be suitable. Such focusing apparatus may include grazing incidence mirrors, Fresnel zone plates, and synthetic multilayer devices of alternating high and low density material (e.g., tungsten and carbon). In each case, the reflector is curved to focus the diffracted x-rays onto the specimen.

A suitable arrangement of components for the analysis instrument 71 is based on the conventional Rowland circle 46. In this arrangement, the anode surface 22, the crystal 34, and the film surface 12 are substantially on the circle, for example, as taught in U.S. Pat. No. 3,772,522, to Hammond et al., issued 13 Nov. 1973 and entitled "Crystal Monochromator and Method of Fabricating a Diffraction Crystal Employed Therein."

The x-rays 36 cause photoelectrons 52 to be emitted from the selected active pixel area of an analysis volume, e.g., the film 2 and portion of underlying substrate. The electron energies generally include a low energy peak in the range of up to 10 eV, usually about 2 to 5 eV, plus higher kinetic energy peaks or lines characteristic of chemical species (e.g., chemical elements and/or their electron bondings) in the selected pixel area. In the case of rastering, the characteristic photoelectrons vary with any varying chemistry across the array of pixel areas, and the low energy electrons (commonly known as "secondary electrons") vary with topography, as well. Detection and/or analysis of the photoelectrons are used to provide information (e.g., spectral data) regarding the film at a selected pixel area or across the rastered array of areas of the film. There also may be Auger electrons which, for the present purpose, are included in the term "photoelectrons" as they are caused by the x-rays.

In one embodiment of the invention, an electron energy analyzer 54 receives a portion of the photoelectrons 52. The analyzer may be a known or desired type, generally either magnetic or electrostatic, which deflects the photoelectrons in a predetermined path 68 according to electron energy and then to a detector 70. A selected control, generally an electrical signal (current or voltage), is applied to the deflector to establish the amount of deflection and so is representative of selected energy of photoelectrons deflected in the predetermined path. In a magnetic analyzer such as a magnetic prism, a current signal through the magnet coils is appropriately selected, and in an electrostatic analyzer a deflecting voltage signal is selected.

The electrostatic lens system 56 may be any conventional lens, for example, a PHI Omnifocus IV™ lens available from Physical Electronics Inc. The lens should include pairs of orthogonal deflection plates with applied voltages from a source 62. The voltages are selected, varied, or oscillated via the processor 76 in cooperative synchronization with positioning or rastering of the primary electron beam 20, under control of the processor, to centralize off-axis photoelectrons so that a substantial portion of the electrons reach the slit 84 and enter into the analyzer 54.

Continuing still with FIG. 3, with a selected voltage from a voltage source 62 applied via lines 69 across the hemispheres 64, 66 of the analyzer, electrons of selected energy travel in a narrow range of trajectories 68 so as to exit the analyzer into the detector 70. The latter may be a conventional multichannel detector, for example, having 16 channels for detecting a small range of electron energies passed by the analyzer in slightly different trajectories. A further lens (not shown) may be placed between the analyzer and the detector, if desired or required for certain types of detectors.

Signals from the detector 70 corresponding to intensity of photoelectron input are carried on a line or lines 72 (via an appropriate amplifier, not shown) to an analyzing portion 74 of the processing unit 76, which combines control electronics and computer processing. The processing provides electron energy information and thereby information on components that are present and emitting the photoelectrons from the particular film surface area.

The information is stored, displayed on a monitor 78, and/or printed out in the form of images, numbers, and/or graphs. By cooperating the display (which herein includes the processing) with the electron beam directing means 28, 30, via line 80 from the processor to the controller 30, a mapping of the components in the selected or scanned surface area is effected and displayed. The mapping provides surface information corresponding to the selected pixel area location, or the rastered array of pixel areas on the film surface.

Other portions of the instrument 71, such as the secondary electron detector 88 and electron gun 98 providing ions 100, are used as described in U.S. Pat. No. 5,315,113.

When a sample film is placed into the analysis system, a spectrum is obtained which typically has several spectral peak shape(s) representative of one or more components of a particular type of film (e.g., $O_{1s}$, $Si_{4+}$, $N_{1s}$, etc., irradiated and detected from a film). A particular process defined by a predefined set of processing conditions typically forms the film. For example, the particular process may be a process used in a manufacturing line for the formation of a thin gate oxide film formed on a silicon substrate in the manufacture of integrated circuits. Such measured spectral peak shapes may be, for example, peak shapes associated with silicon in the gate oxide film and the silicon in the substrate upon which the film is formed when the film is silicon oxynitride film formed on a silicon substrate. Generally, the relative area under each of the peak shapes gives the relative abundance of the component in the analysis volume, e.g., in the film and at least a portion of the underlying substrate to a particular depth. The peak shapes are typically expressed as an intensity value. Also, a suitable function is typically used to extract the intensity value for a peak shape. When the peak shapes overlap, such suitable function may include a basis function or the use of a basis spectrum. Typical functions to extract peak intensities include basis function, slope determination, peak area determination, etc., which are known in the art.

Figure 4:
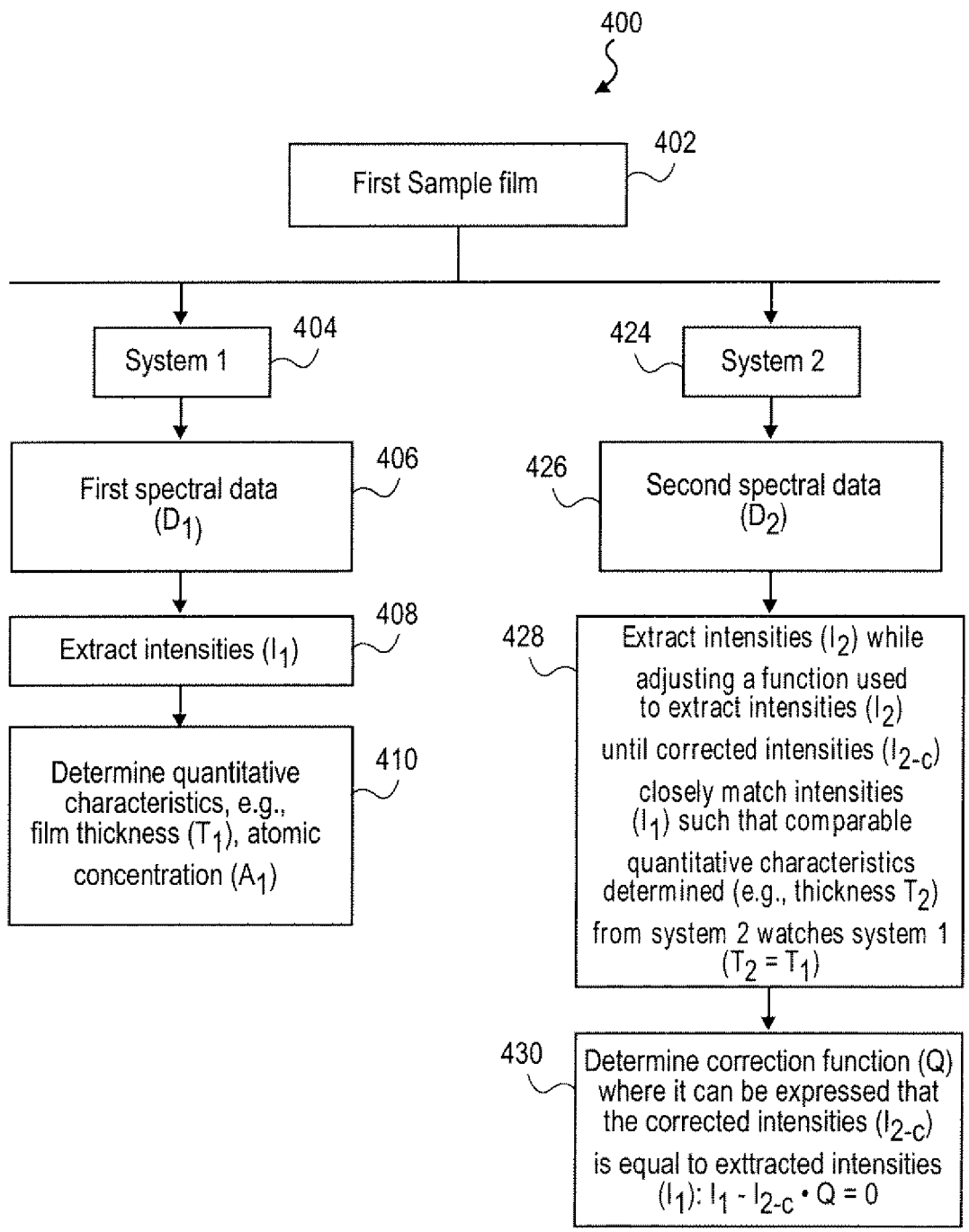
FIG. 4 illustrates an exemplary method of calibrating multiple systems to one another according to the present invention.

In one embodiment of the present invention, the data from a system 1 and the data from a system 2 are minimized to one another by using an adjusted function. For instance, the shape of the fits, the basis functions, or other functions used to extract the intensities of the spectral peaks are adjusted until the characteristic measurements determined using the intensities (e.g., thickness) are in agreement. In other words, intensities extracted for the elements in the film are obtained by adjusting the shape function or fit (e.g., basis function) used to extract such intensities from the raw spectral data until intensities extracted from the system 2 would closely match the intensities extracted from the system 1. Transmission correction factors are determined (possibly or optimally simultaneously) so that the intensities of two systems can be equal to one another. For computation of quantitative characteristics which involve only ratios of intensities, the determination of the shape of the transmission correction factor as a function of electron energy relative to the control system is sufficient. The extracted intensities (adjusted/corrected) are then used for film characteristic determination. The characteristic measurements obtained from system 2 thus match the measurements obtained from system 1 for a particular film and a particular characteristic measurement FIG. 4 illustrates an exemplary method 400 according to embodiments of the present invention. In one embodiment, a film (box 402) is placed in the system 1 at box 404. The system 1 can be an XPS system as previously described. A first spectral data ($D_1$) is obtained (e.g., as previously described) for the film at box 406. The film can be a dielectric film such as a silicon oxynitride film or silicon dioxide and may have a thickness of less than about 10 nanometers, and even less than about 4 nanometers. The film is formed on a substrate (e.g., silicon containing material or silicon wafer). In one embodiment, the spectrum includes a spectral peak shape representative of at least one component (or elemental species) in the film and at least an additional spectral peak shape representative of a component in the substrate. In the embodiment with the silicon dioxide film ($SiO_2$), the spectrum may include peak shapes representatives of $O_{1s}$ from the $SiO_2$ film, $Si_{4+}$ from the $SiO_2$ film, and $Si_{2p}$ from the substrate. In the embodiment with the silicon oxynitride film (SiON), the spectrum may include peak shapes representatives of $O_{1s}$, $Si_{4+}$, and $N_{1s}$ from the SiON film, and $Si_{2p}$, from the substrate.

Suitable functions (e.g., a basis function) are used to extract intensities from the first spectral data ($D_1$) to provide a first set of extracted intensities ($I_1$) at box 408. A first quantitative characteristic associated with the first sample film is determined using the first set of extracted intensities at box 410. In one embodiment, film thickness ($T_1$) is determined for the film. Atomic concentrations ($A_1$) for the components in the film can also be determined depending on applications. Methods of determining a quantitative characteristic using extracted intensities such as film thickness or component atomic concentration are known in the art. In the example where the film is $SiO_2$, the intensities to be extracted also include intensities representative of $O_{1s}$ from the $SiO_2$ film, $Si_{4+}$ from the $SiO_2$ film, and $Si_{2p}$, from the substrate. The film thickness for the $SiO_2$ film can be determined using intensity ratio values of the Si intensity form the substrate and the Si intensity from the $SiO_2$ film. An exemplary thickness determination method is also provided below.

In one embodiment a system 2 (box 424) is calibrated to the system 1 with the system 1 acting as the control system. The system 2 can be an XPS system as previously described, or similar to the system 1 with some hardware or component configuration differences.

At box 426, a second set of spectral data ($D_2$) associated with a comparable sample film measured by a second photoelectron spectroscopy system is obtained. The comparable film can be the same or identical film as the first sample film that was tested in the system 1 and now placed in the system 2. Thus, the comparable sample film can be the same sample as the first sample film or another film that can be compared to the first sample film (e.g., SiON or $SiO_2$). The same functions that are used and applied to the first spectral data ($D_1$) are used and applied to the second set of spectral data ($D_2$) to extract intensities ($I_2$) at box 428. However, on the second set of data, each function is continually adjusted as they are being applied to the spectral peaks. As to be understood, the intensities to be extracted would be for the same elemental species extracted form the first spectral data ($D_1$). Thus, in the example of the $SiO_2$ film, the intensities extracted and adjusted form the spectral data $D_2$ may include intensities representative of $O_{1s}$ from the $SiO_2$ film, $Si_{4+}$ from the $SiO_2$ film, and $Si_{2p}$, from the substrate. Herein, the term "representative intensity" may be used to indicate the same type of intensity for the same elemental species of the same type of film. A second set of corrected extracted intensities thus comprises the intensities extracted form the spectral data $D_2$ using adjusted functions.

At box 428, a second quantitative characteristic for the comparable sample film is determined using the second set of corrected-extracted intensities ($I_{2-c}$). It is optimal that the suitable functions are continually adjusted until the determined second quantitative characteristic closely or substantially matches the first quantitative characteristic. For example, when the first set of intensities is used to determine a film thickness for the sample film, the second set of intensities is extracted with the adjusted functions such that when the second set of corrected-extracted intensities is used to determine the same film thickness, the results will be the same. Thus, for example after the intensities ($I_{2-c}$) are extracted using the adjusted function, the thickness $T_1$ is equal to $T_2$ for a particular film (e.g., $SiO_2$ formed on an Si substrate)

In one embodiment, after the intensities ($I_{2-c}$) are extracted, a transmission correction factor (Q) is determined for each of the intensities ($I_{2-c}$). The transmission factor Q is a factor that would allow the intensity ($I_{2-c}$) to be equal to ($I_1$). In other words, $$I_1 - I_{2-c} * Q = 0 \tag{1}$$

When the intensities from the system 2 are extracted with adjusted functions, the intensities may be close or substantially close to those extracted for the system 1. The transmission correction factors will be values or numbers that equate one extracted intensity to another.

With the method 400, the system 2 is calibrated to system 1. This process can be performed for multiple elemental species that can possibly appear and detected by the system in a film of interest. For instance, the method 400 can be performed for the $Si_{4+}$, $O_{1s}$, $N_+$ and $N_{1s}$ in a SiON film. An adjusted functions is determined for each one of the elemental species. A transmission correction factor is also determined for each of the elemental species. Subsequent films having the same elemental species to be characterized using the system 2 can utilize the same adjusted functions and transmission correction factors applied to the originally obtained spectral data during the intensity extraction process (at box 428). For elemental species not analyzed using the method 400 above, the adjusted functions and the transmission correction factors can be interpolated or slightly extrapolated from the actually collected data using the method 400. For example, a subsequent film to be characterized by the system 2 can have its intensities extracted using the adjusted functions and corrected by the transmission correction factors to obtain intensities that can be said to be equal to the control system without being actually measured on the control system. For cases where the desired quantitative characteristics involve only ratios of intensities, such as film thickness, or atomic concentrations, then it is not necessary for equation 1 to hold for such characteristics to match between systems, but rather the interpolated and extrapolated shape of the correction factor Q in box 430 be determined as a function of photoelectron energy with the overall magnitude factoring out of the ratio.

FIGS. 5-7 illustrate an interpolation and extrapolation method that can be used to obtain a transmission correction factor for elemental species that are not analyzed during a tool matching method (method 400).

In one embodiment (FIG. 5), a film $SiO_2$ formed on a silicon substrate was characterized using the method 400. A spectrum 1 is obtained from system 1 and another spectrum 2 is obtained from system 2. FIG. 5 illustrates an exemplary spectrum that may be obtained from both systems 1 and 2. In this example, system 1 acts as the control system and system 2 is to be calibrated to the system 1. Intensities are extracted for both spectral data obtained from the systems 1 and 2 as previously described in method 400. A peak 502 representative of the $Si_{2p}$ species from the substrate is obtained at binding energy 99.75; a peak 504 representative of the Si photoelectron species that is affected by interaction with the oxygen in the $SiO_2$ film, indicated as $Si_{4+}$ peak, is obtained at binding energy 103; and a peak 506 representative of the $O_{1s}$ peak from the Oxygen species in the $SiO_2$ film is obtained at binding energy 535.

With the spectrum 1, the intensities for each peaks 502, 504, and 506 are extracted using a particular function for each peak and the intensities indicate the integrated detector count as a function of binding energy for each peak. The function can be a basis function typically used to extract intensities for overlapping peaks (e.g., peaks 502 and 504 for the $Si_{2p}$ from the substrate and the $Si_{4+}$ from the $SiO_2$ film). Simple integration or calculating the area under the peak 506 will give the intensity for the peak 506, which has no overlapping peak.

For the spectrum 2, the functions used to extract the peaks 502, 504, and 506 are adjusted accordingly so that the intensity for each peak can be minimized to the respective intensity extracted from the spectrum 1. In other words, the functions used to extract the intensities for the spectrum 2 are adjusted so that the shapes of the peaks can be as close to the shapes of the peaks obtained for the spectrum 1. In one embodiment, a transmission correction factor is simultaneously determined for each extracted intensity value for the spectrum 1. As previously mentioned, $$I_1 - I_{2\text{-}c} * Q = 0 \tag{1}$$

Q represents the transmission correction factor;

$I_1$ represents the intensity value obtained from the spectrum 1; and $I_{2\text{-}c}$ represents the intensity value obtained form spectrum 2.

Therefore, for each extracted intensity from the spectrum 2 using an adjusted function, a transmission value is determined simultaneously. The adjustment stops when the equation (1) is satisfied. Once the transmission correction factor is determined, it is stored and used for subsequent film characterized by the system 2.

In FIG. 6, the transmission correction factor determination for Si and oxygen species from the $SiO_2$ film are determined in one example. As an illustration, from the system 1, a basis function is applied to the spectrum 1 and an extracted intensity value for the $Si_{4+}$ from the $SiO_2$ film of 47.5 is obtained. From the system 2, the same basis function used while the basis function is adjusted by a certain factor toward minimizing the difference between the peak shape of the spectrum 1 and the peak shape of the spectrum 2. An extracted intensity value of 50 is obtained using the adjusted basis function. Simultaneously with the basis function adjustment, the transmission correction factor is also determined using equation (1). In this particular example, the transmission correction factor is 0.95. A similar process is performed to the peaks for Oxygen species and from system 1, the intensity value for the oxygen is 200 while from system 2, the intensity value for the Oxygen is 190. Similarly, the transmission correction factor is simultaneously determined to be 1.05. The same process is performed for other species in the film.

In FIG. 7, the transmission correction factors are plotted against the binding energy (BE) spectrum. A correlation function and best-fit curve can be determined and from the curve 700, transmission correction factors for other species covered by the BE spectrum range can be interpolated or slightly extrapolated. It is thus optimal that as many films and the components of the films be characterized in both systems as possible to cover a broad range of possible transmission correction factors and adjusted functions.

Figure 13:
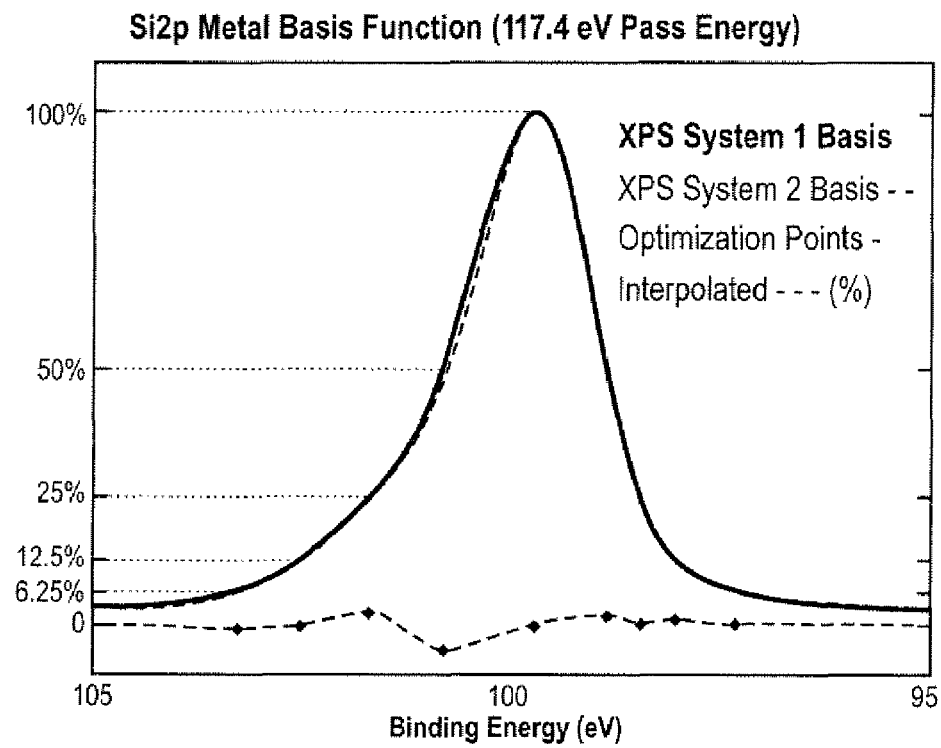
FIG. 13 illustrates an exemplary spectral peak being adjusted to match a respective spectral peak obtained from a control system.

FIG. 13 illustrates in more detail an exemplary basis function adjustment technique that can be used for embodiments of the present invention. The raw spectral data from an XPS system consist of measured quantities that are derived of equal length arrays corresponding to photoelectron energy and the number of electrons detected per second, or intensity, at that energy. When plotted against the energy, the intensity array has peaks characteristic of atomic photoelectron emission for each element present in the film and substrate induced by a narrow energy X-ray beam and broadened by transmission through the analyzing section of the XPS system.

In the example of a thin film SiO2 or SiNO on a silicon wafer substrate, two overlapping silicon peaks are observed: one form the substrate corresponding to pure silicon metal and one with a slightly lower electron energy peak for silicon which has bonded, typically in a 4+ configuration, with oxygen or nitrogen present in the film. The energy separation of the two peaks, together with the energy resolution broadening from the XPS system is such that the peaks always overlap some, and require peak fitting deconvolution algorithm to determine the individual intensities.

The accuracy of the silicon peak intensity deconvolution is of particular importance in thin film characterization using XPS systems, as it is typically the ratio of the intensities of these two states which is used to determine the film thickness. A method found to produce the smallest statistical fluctuation in the resultant intensities has be to use different tabulated peak shapes known as "basis spectra" for each state, which are simultaneously fit to the two peak system where only two operations are permitted on the basis spectra: shift in energy and broadening by convolution with a Gaussian distribution.

In order to minimize the transmission correction factor, or to minimize intensities extracted for the same spectrum measure on two systems, some aspect of the measured spectra or the basis spectra must be changed between the two systems. In one embodiment, the silicon basis spectra line shapes used on the system 2 is adjusted by a very small amount relative to the system 1. In one embodiment, and as shown in FIG. 13, the $Si_{2p}$ species from the silicon substrate is adjusted.

FIG. 13 shows two peaks representative of the $Si_{2p}$ species, one from an XPS system 1 and one from an XPS system 2. Adjustment points are made along the peak area of the spectrum from the XPS system 2 to minimize the difference between the two spectra. Thus, the basis function for the spectrum from the XPS system 2 is adjusted. In the example of FIG. 13, correction points for the peak are varied with $\pm\frac{1}{2}$, $\pm\frac{1}{4}$, $\pm\frac{1}{8}$, and $\pm\frac{1}{16}$ peak value until the thickness determination using the extracted intensities from the two systems can be matched. In other words, the correction points for the peak are varied with $\pm\frac{1}{2}$, $\pm\frac{1}{4}$, $\pm\frac{1}{8}$, and $\pm\frac{1}{16}$ peak value until the extracted intensities are minimized to one another. Simultaneously with the peak correction point process, a transmission correction factor can be determined for the extracted intensity and corrected from the system 2 to equate the intensity to the that extracted from the system 1. When the transmission correction factor is the smallest, the adjustment may stop. The simultaneous transmission correction factor determination enable an efficient correction process for extracting the intensity from the system 2 with the smallest difference to the intensity extracted from system 1.

Figure 14:
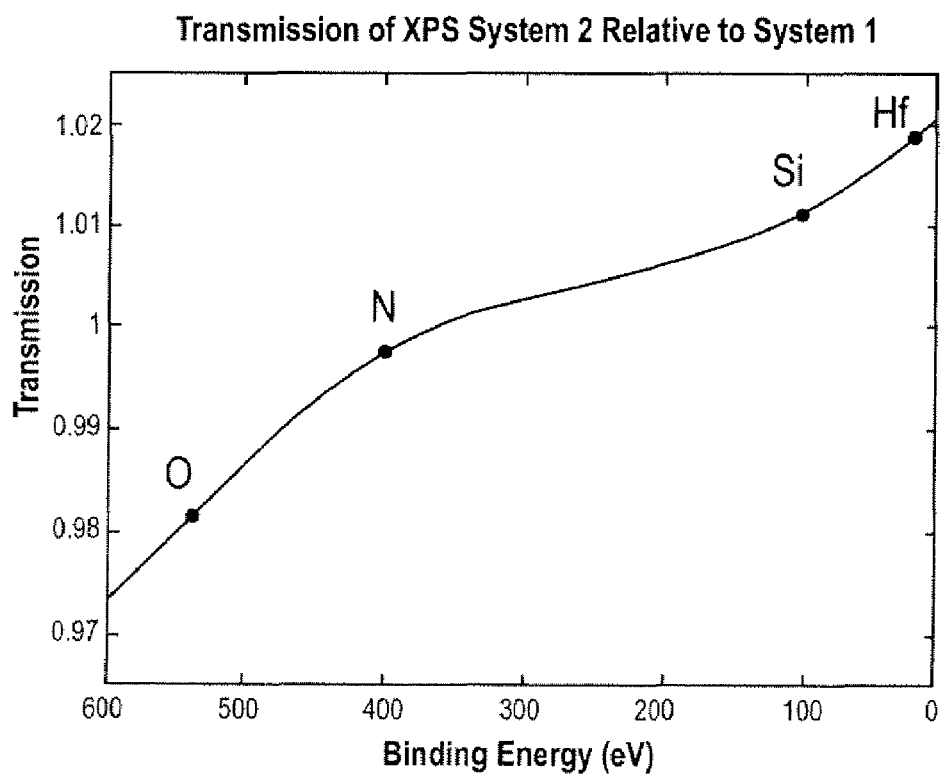
FIG. 14 illustrates a method of interpolating or extrapolating transmission correction factors for elemental species using a set of transmission correction factors determined for measured sample films on two systems.

FIG. 14 illustrate an example of transmission correction factors plotted against the elemental species binding energy. The plot shown in FIG. 14 can be used to interpolate transmission correction factors for other elemental species in other films. In this example, transmission correction factors are determined for elemental species including oxygen, nitrogen, silicon and hafnium that were analyzed using both systems 1 and 2 and having the respective intensities minimized. An interpolation curve is shown between the points so that other elements intermediate to the binding energies where the transmission correction was explicitly determined may take their transmission correction factor from the curve. The plot shown in FIG. 14 is also an example of the case where the practitioner is only interested in characteristic measurements of film properties formed by intensity ratios such as film thickness or relative atomic concentrations of all element, so that the absolute magnitude of the curve factors out and is thusly shown plotted about a mean value of 1.

Figure 8:
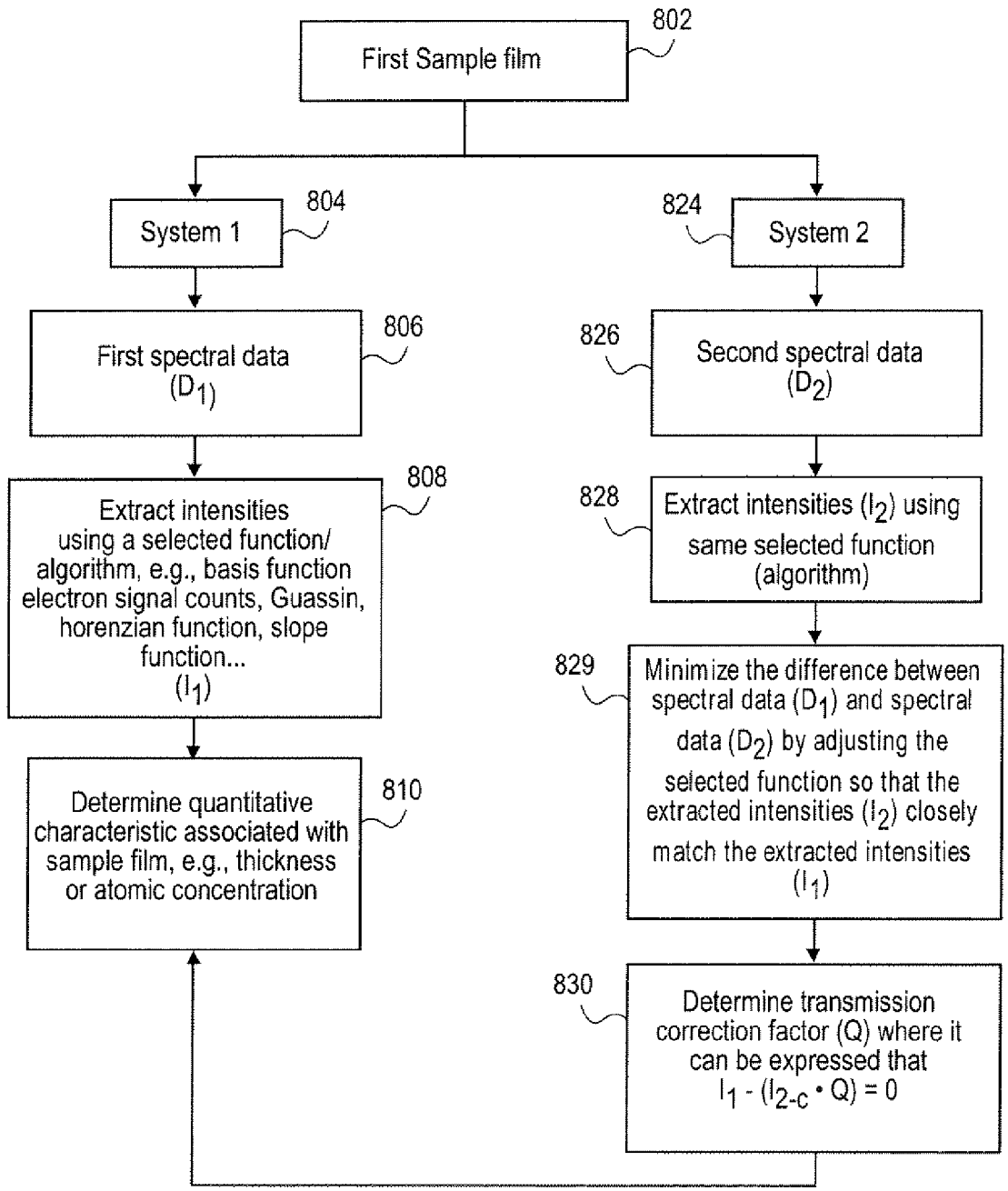
FIG. 8 illustrates another exemplary method of calibrating multiple systems to one another according to the present invention using minimization between measurements from the spectral data.

FIG. 8 illustrates another exemplary method 800 of characterizing a film with a calibrating capability for multiple systems according to embodiments of the present invention. Method 800 is similar to method 400 above with the addition of using a minimization function to match the intensities from the spectrum 2 to the intensities from the spectrum 1.

Similar to above, a film (box 802) is placed in the system 1 at box 804. The system 1 can be an XPS system previously described. A first spectral data ($D_1$) is obtained for the film at box 806. Suitable functions (e.g., a basis function) are used to extract intensities for one or more elemental species associated with the sample film to provide a first set of extracted intensities ($I_1$) at box 808. The selected functions can be a basis function, electron signal count determination, Gaussian function, Lorentzian function, and a slope determination function. A first quantitative characteristic associated with the first sample film is determined using the first set of extracted intensities at box 810. In one embodiment, film thickness is determined for the film. Atomic concentration for the components in the film can also be determined depending on applications. Methods of determining a quantitative characteristic using extracted intensities such as film thickness or component atomic concentration are known in the art.

In one embodiment a system 2 (box 824) is calibrated to the system 1 with the system 1 acting as the control system. The system 2 can be an XPS system as previously described.

At box 826, a second set of spectral data ($D_2$) associated with a comparable sample film measured by a second photoelectron spectroscopy system is obtained. The comparable film can be the same or identical film as the first sample film that was tested in the system 1. Thus, the comparable sample film can be the same sample as the first sample film or another film that can be compared to the first sample film. The same functions that are used and applied to the first spectral data ($D_1$) are used and applied to the second set of spectral data ($D_2$) to extract intensities ($I_2$) at box 828. However, on the second set of data, the functions are continually adjusted as they are being applied to the spectral peaks as previously described. A second set of corrected-extracted intensities ($I_{2-c}$) thus comprises the intensities extracted form the spectral data $D_2$ using the adjusted functions. The intensities from the spectral data $D_2$ and $D_1$ are thus minimized to one another.

At box 830, a transmission correction factor (Q) for each of the extracted intensities ($I_{2-c}$) is determined (for quantitative characteristics which involve only ratios of intensities the determination of the shape of the transmission correction factor as a function of electron energy relative to the control system is sufficient). Then, the characteristic for the comparable sample film is performed using the second set of corrected-extracted intensities ($I_{2-c}$) that have also been corrected by the transmission correction factors. It is optimal that the selected function is continually adjusted until the determined second quantitative characteristic closely or substantially matches the first quantitative characteristic. For example, when the first set of intensities is used to determine a film thickness for the sample film, the second set of intensities is extracted with the adjusted function such that when the second set of corrected-extracted intensities is used to determine the same film thickness, the results will be the same. Thus, for example, after the intensities ($I_{2-c}$) are extracted using the adjusted function and corrected by the transmission correction factors, the thickness of the film measured in system 2 will be equal to the thickness of the film measured in system 1.

Figure 9:
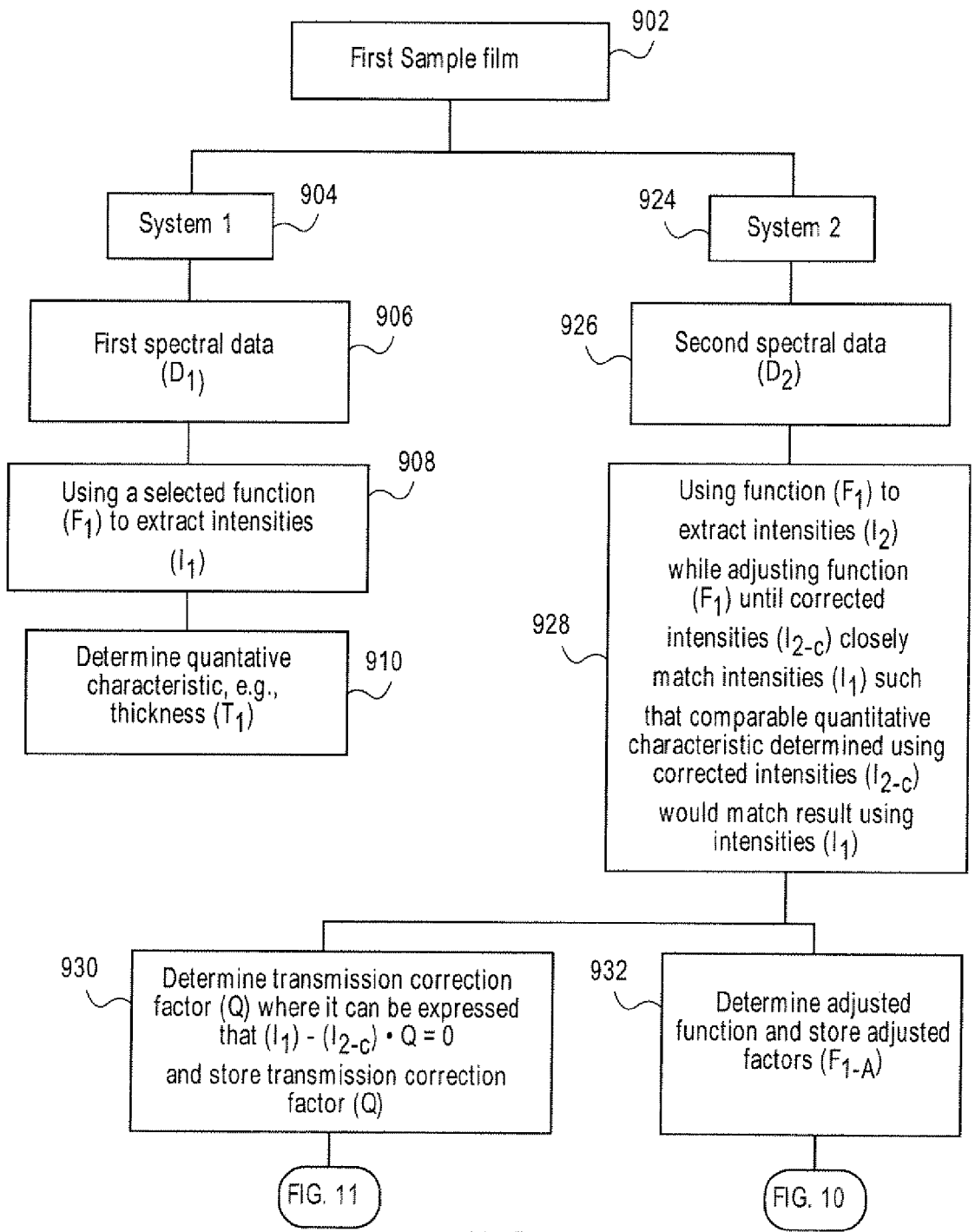
FIGS. 9-11 illustrates an exemplary method of characterizing a film while calibrating multiple systems to one another according to the present invention.
Figure 10:
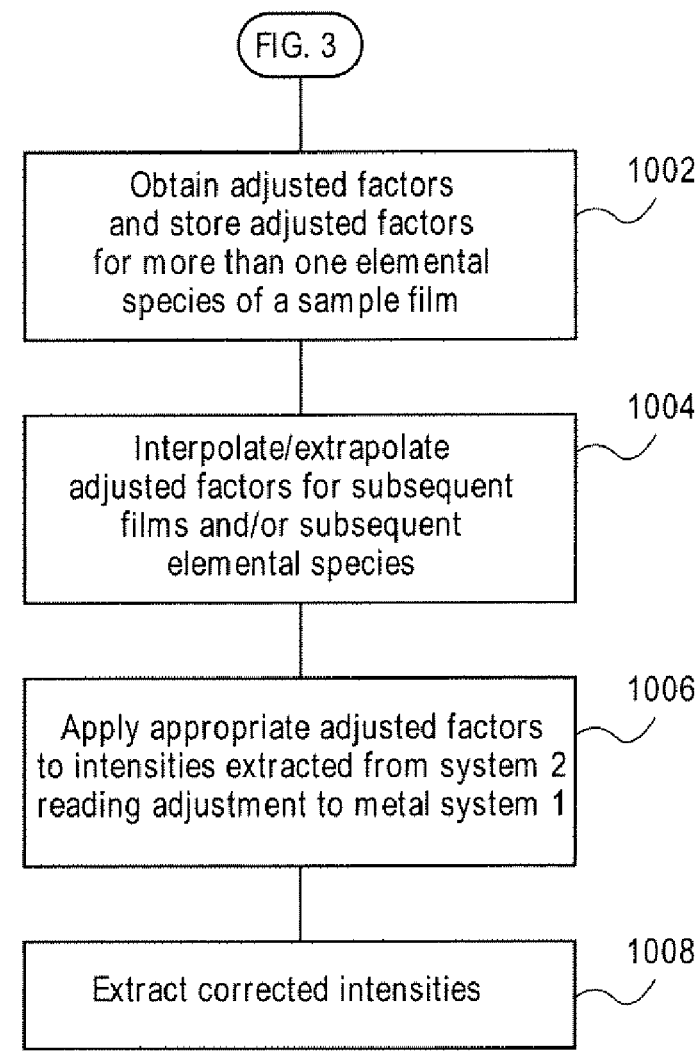
Figure 11:
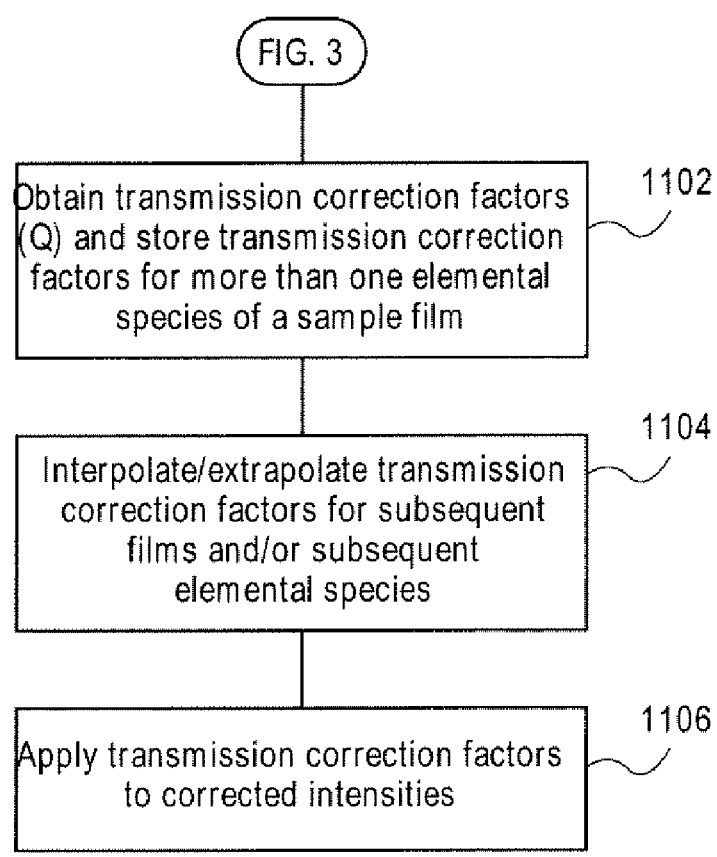

FIGS. 9-11 illustrate an exemplary method 900 of characterizing film(s) on a system and calibrating that system to a control system and using correction factors on subsequent films measured on such system. The method 900 can be written into a program and installed or incorporated into a device so that it can be ran by the computer apparatus of the analysis system such as the computer apparatus 13 of the XPS system 1. In general, to incorporate the method 900, the system 1 or system 2 is configured with a computer apparatus that is able to recognize a spectral peak shape of the acquired spectrum of at least one component of the film. The computer apparatus is also able extract one or more intensity values associated with the acquired spectrum using suitable functions as previously described. Each selected shape function is adjusted until the extracted intensity value is in agreement with a control intensity value extracted from a control spectrum using the same selected shape function. The computer apparatus is also able to select a suitable function, adjust the function, and store the adjusted shape function for an elemental species. The adjusted shape function is obtained when the extracted intensity value is in agreement with the control intensity value. The computer apparatus is also able to determine a transmission correction factor that can be applied to each extracted intensity to equate that intensity to a respective intensity of the control spectrum and store the transmission correction factor for an elemental species determined (for quantitative characteristics which involve only ratios of intensities the determination of the shape of the transmission correction factor as a function of electron energy relative to the control system is sufficient). The computer apparatus is also able to determine at least one quantitative measurement for the film using the extracted intensities, adjusted intensities, or corrected intensities.

Further yet, the computer apparatus is able to select, interpolate, or extrapolate form the stored adjusted functions and/or transmission correction factors for elemental species of subsequent films characterized by the system 1 or 2.

Turning now to the method 900, a first sample film (box 902) is placed in a system 1 at box 904. The system 1 can be an XPS system previously described with a computer apparatus capable of executing a program to carry out the method 900. A first spectral data ($D_1$) is obtained for the film at box 906. The spectral data ($D_1$) may include several elemental species peaks. A selected suitable function $F_1$ (e.g., a basis function) is used to extract an intensity for each peak representative of each elemental species associated with the sample film to provide a first set of extracted intensities ($I_1$) at box 908. A first quantitative characteristic thickness ($T_1$) associated with the first sample film is determined using the first set of extracted intensities at box 910. Atomic concentration for the components in the film, etc., can also be determined depending on applications. In one embodiment, the XPS system 1 is equipped with a computer apparatus that can execute a program to carry out the process described.

In one embodiment a system 2 (box 924) is calibrated to the system 1 with the system 1 acting as the control system. The system 2 can be an XPS system as previously described. The system 2 includes a computer apparatus configured to execute the program that can carry out the method 900. The first sample film is one with known values, for example, known thickness values with known components (e.g., known by characterization using the system 1 or by other means).

At box 926, a second set of spectral data ($D_2$) associated with the first sample film measured by the second photoelectron spectroscopy system is obtained. The spectral data ($D_2$) includes the same elemental species peaks as that of data ($D_1$). The same selected suitable functions ($F_1$) used for the first set of spectral data ($D_1$) are now applied to the second set of spectral data ($D_2$) to extract intensities ($I_2$) at box 928. However, on the second set of data, each function is continually adjusted so that the respective intensity is as close as possible or matches each respective intensity of the intensities $I_1$. The second set of corrected-extracted intensities ($I_{2-c}$) thus includes the intensities extracted using the adjusted functions. The intensities from the spectral data $D_2$ and $D_1$ are thus minimized to one another.

At box 930, a transmission correction factor (Q) for each of the extracted intensities ($I_{2-c}$) is determined and stored. At box 932, an adjusted function value used to obtain each of the extracted intensities ($I_{2-c}$) is determined and stored (for quantitative characteristics which involve only ratios of intensities the determination of the shape of the transmission correction factor as a function of electron energy relative to the control system is sufficient). In one embodiment, the transmission correction factor and the adjusted function value are stored so that the computer apparatus can access them. In one embodiment, the computer apparatus is able to select, determine, interpolate, or extrapolate appropriate adjusted functions and transmission correction factors for particular elemental species in a subsequent film from the stored values.

The method 900 continues to FIGS. 10-11. In one embodiment, at box 1002, adjusted functions (factors) are obtained and stored for more than one elemental species of the sample film. In one embodiment, multiple sample films are characterized under both the system 1 and system 2 as previously discussed. A plurality of adjusted functions are determined and stored for all of the possibly known components in the sample films that are characterized under both systems 1 and 2.

At box 1004, one or more adjusted functions are interpolated or extrapolated from the collected samples. For example, for a particular film or elemental species of a film that was not characterized under the systems 1 and 2 so that the actual adjusted factor or function was not determined by the process previously described, an adjusted factor or adjusted factors to be used to extract intensity values can be interpolated or extrapolated from the collected values as previously discussed. For example, if adjusted factors were determined for the elemental species in an $SiO_2$ film at BE 103 and 535, a best-fit curve is determined and an adjusted factor for a species falling within the BE spectrum of 103-535 can be interpolated from the actually collected data. Then, at box 1006, an appropriate adjusted factor is applied to a spectrum for a particular film or elemental species of a film measured using the system 2 to extract intensity value for the particular film measured using the system 2. At box 1008, one or more corrected intensity values are obtained for the particular film.

Continuing to FIG. 11, in one embodiment, at box 1102, transmission correction factors are obtained and stored for more than one elemental species of the sample film. In one embodiment, multiple sample films are characterized under both the system 1 and system 2 as previously discussed. A plurality of transmission correction factors are determined and stored for all of the possibly known components in the sample films that are characterized under both systems 1 and 2.

At box 1104, one or more transmission correction factors are interpolated or extrapolated from the collected samples. For example, for a particular film or elemental species of a film that was not characterized under the systems 1 and 2 so that the actual transmission correction factor was not determined by the process previously described, a transmission correction factor or transmission correction factors to be used to extract intensity values can be interpolated or extrapolated from the collected values as previously discussed. For example, if transmission correction factors were determined for the elemental species in an $SiO_2$ film at BE 103 and 535, a best-fit curve is determined and a transmission correction factor for a species falling within the BE spectrum of 103-535 can be interpolated from the actually collected data. Then, at box 1106, an appropriate transmission correction factor is applied to an intensity value for an elemental species of a particular film or elemental species of a film measured using the system 2. Following this step, film characteristics can be determined using the corrected intensity.

Figure 12:
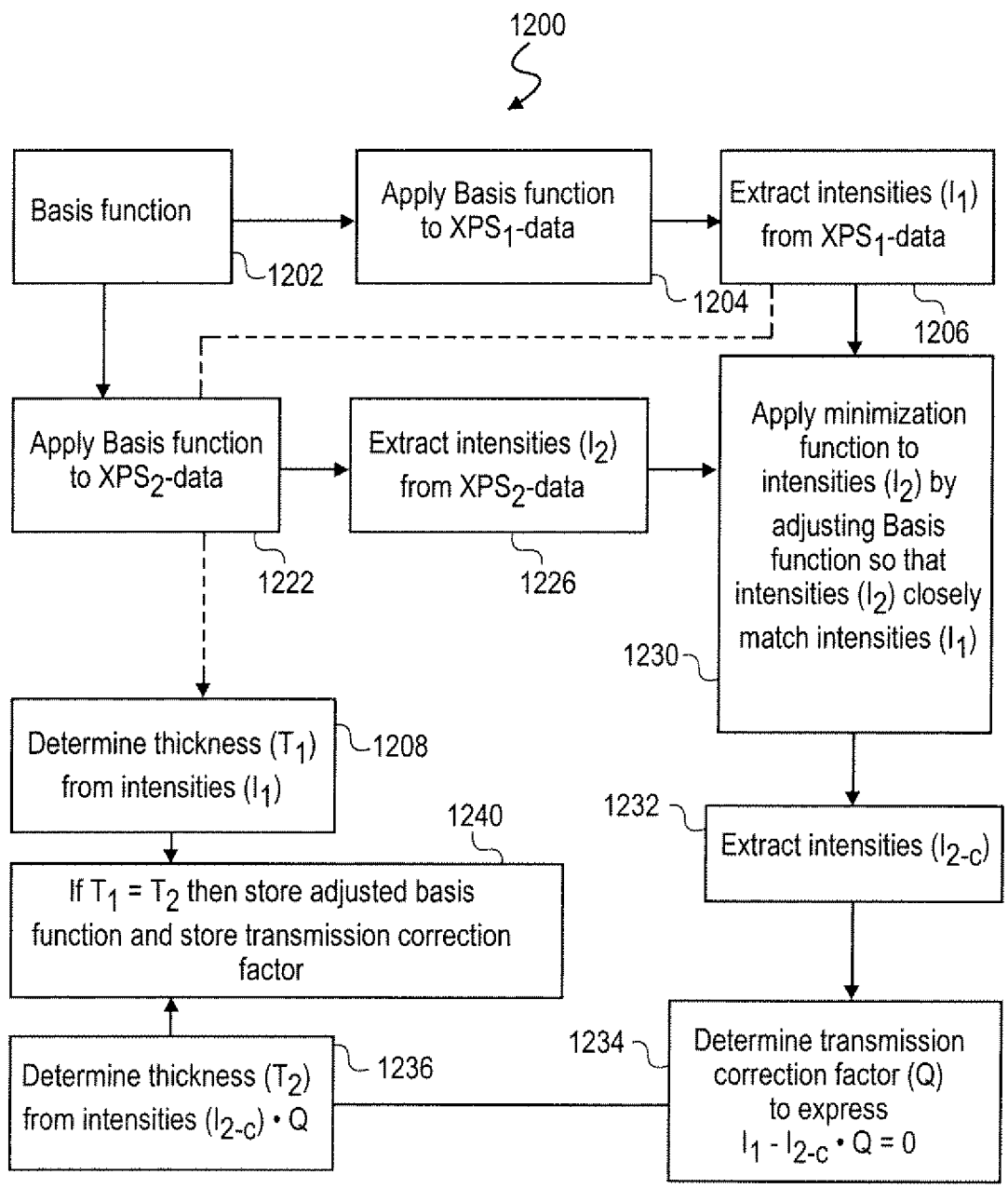
FIG. 12 illustrates an exemplary process of analyzing a film while matching multiple systems to one another according to the present invention.

FIG. 12 illustrates an exemplary process 1200 of matching two XPS systems to each other. It is to be noted that multiple XPS systems can also be matched to one another using similar process. For instance, after XPS system 2 is matched to XPS system 1, XPS system 3 can be matched to either system 1 or 2 using similar process.

In the process 1200, two spectra are obtained from an XPS system 1 and an XPS system 2, $XPS_1$-data and $XPS_2$-data. At 1202, a basis function is provided. At 1204, the basis function (or other suitable intensity extraction function) is applied to the $XPS_1$-data. At 1206, a first set of intensities ($I_1$) is extracted from the $XPS_1$-data. At 1208, a film thickness ($T_1$) is determined using the first set of intensities ($I_1$). Method of determining a film thickness using intensities are known in the art and also summarized below.

Also in the process 1200, at 1222, the same basis function is provided. At 1224, the basis function is applied to the $XPS_2$-data. At 1226, a second set of intensities (I2) is extracted from the $XPS_2$-data. At 1230, the second set of intensities ($I_2$) is minimized to the first set intensities ($I_1$). In one embodiment, the basis function is adjusted (can be adjusted continually) so that the spectral peak shapes from the $XPS_2$-data closely or substantially match the spectral peak shapes from the $XPS_1$-data. In that way, the intensities ($I_2$) extracted can be corrected to closely match the intensities ($I_1$). At 1232, a corrected set of second intensities ($I_{2-c}$) is obtained. At 1234, a transmission correction factor is determined for each value of the corrected second set of intensities film thickness ($I_{2-c}$). For each corrected intensity value ($I_{2-c}$), the equation: $I_1-(I_{2-c})=0$ must be true. At 1236, film thickness ($T_2$) is determined using the corrected second set of intensities film thickness ($I_{2-c}$). At 1240, it is determined that if film thickness ($T_2$) is equal to film thickness (T1), then an adjusted basis function that was used to extract each of the corrected second intensities ($I_{2-c}$) is stored. Also, at 1240, the transmission correction factor is also stored for subsequent uses. In one embodiment, the process may include a step of correlating all of the transmission correction factors to appropriate BE values within a spectrum range so that interpolation or extrapolation can be performed for other elemental species. Similarly, the process may include a step of correlating all of the adjusted basis function to appropriate BE values within a spectrum range so that interpolation or extrapolation can be performed for other elemental species.

It has been previously mentioned that film thickness is used to characterize a film in multiple systems according to embodiments of the present invention. The section below summarizes an exemplary method of film thickness determination. It is to be understood that other method can also be used. The below technique uses intensity ratio values of two elemental species to determine film thickness.

In one embodiment, a film to be characterized is SiON formed on a Si substrate. In one embodiment, peak intensity values from the film, $Si_{4+}$, and substrate, $Si_{2p}$, of the Si2p region of the spectrum for the silicon oxynitride film are used for the calculation of the film thickness. Film thickness of the silicon oxynitride film can be calculated according to the following equation:

$$\text{Film thickness} = \lambda \sin(\theta) \ln[K^*(Si_{4+}/Si_{2p}) + 1 - LCorr] \quad (2)$$

The above film thickness equation is a standard equation used to determine the thickness of a thin layer using XPS surface measurements, with an additional term, LCorr, that compensates for spectral contributions of multiple x-ray lines from nonmonochromated x-ray sources, e.g., magnesium x-ray sources. The values for $\lambda$ and K impact the accuracy but not the precision of the thickness measurement. A value for $\lambda$ can be obtained from IMFP (inelastic mean free path) model calculations using NIST database #71. Such a value for $\lambda$ may be, for example, 34 angstroms. The $\lambda$ value can also be referred to as the effective attenuation length. The angle $\theta$ is the take off angle of the photoelectrons normal to the film surface.

The constant K can be determined by analyzing a silicon oxynitride film of known thickness as determined by, for example, TEM measurements. Such a TEM measurement would be made once for each specific particular process. While the TEM measurement may limit the accuracy of the method, it does not limit precision of measurement, which is desirable. In other words, although accuracy is important, precision in obtaining the same measurement for a particular film over and over again is generally more desirable than whether the actual measurement is correct or not correct, as long as the accuracy is within acceptable limits.

The constant Lcorr can be determined by comparing film thickness results from monochromated and nonmonochromated x-ray sources on the same samples and adjusting the constant to achieve the same thickness result.

The peak area ratio of $Si_{4+}/Si_{2p}$ is thus needed to determine the film thickness.

In one embodiment, the film thickness can also be determined by using a look-up table or a calibration curve of a plurality of known reference films. For example, a plurality of reference films with known thickness are placed into the control XPS system. From a spectrum for each of the reference film, an intensity ratio value is obtained for the $Si_{4+}/Si_{2p}$ peak areas. The intensity ratio values are then plotted against the known thickness values to generate a calibration curve. For a sample film, the intensity ratio value can be obtained then correlated to the calibration curve to determine the thickness of the sample film. The same type of correlation technique can be applied to a look-up table to determine the film thickness.

In one embodiment, a program storage media, readable by a media read apparatus under control of a computer, tangibly embodying a program executable to perform processes described herein for characterizing a film while matching results from the system to a control system is provided.

Embodiments of the present invention provide the ability to characterize a film and its components with tool-to-tool matching capabilities. In other words, with regard to too-to-tool matching, whether measurements are taken on a single particular instrument or whether they are performed on different instruments of the same type, the measurements can be expected to be in agreement among tools or systems.

While the invention has been described in terms of several embodiments, those of ordinary skill in the art will recognize that the invention is not limited to the embodiments described. The method and apparatus of the invention, but can be practiced with modification and alteration within the spirit and scope of the appended claims. The description is thus to be regarded as illustrative instead of limiting.

Having disclosed exemplary embodiments, modifications and variations may be made to the disclosed embodiments while remaining within the spirit and scope of the invention as defined by the appended claims.

I claim:

1. A method of calibrating multiple metrology systems to one another comprising:

obtaining a first set of spectral data measured for a first sample film measured by a first photoelectron spectroscopy system;

using a selected function to extract intensities for one or more elemental species associated with said first sample film to provide a first set of extracted intensities;

determining a first quantitative characteristic associated with said first sample film using said first set of extracted intensities;

obtaining a second set of spectral data measured for a comparable sample film measured by a second photoelectron spectroscopy system, said comparable sample film being one of said first sample film or another film that can be compared to said first sample film;

using said selected function and continually adjusting said selected function to extract intensities for said one or more elemental species associated with said comparable sample film to provide a second set of corrected-extracted intensities; and determining a second quantitative characteristic for said comparable sample, said second quantitative characteristic being of same type to said first quantitative characteristic, and wherein said selected function is continually adjusted until said determined second quantitative characteristic closely or substantially matches said first quantitative characteristic.

2. The method of claim 1 further comprising:

determining a transmission correction factor which when applied to said second set of corrected-extracted intensities allows said second set of corrected-extracted intensities to be equal to said first set of extracted intensities.

3. The method of claim 1 further comprising:
applying said transmission correction factor to subsequent spectral data measured on said second photoelectron spectroscopy system.

4. The method of claim 1 further comprising:
determining an adjusted function based on how the selected function is continually adjusted in order to extract said second set of corrected-extracted intensities.

5. The method of claim 1 further comprising:
applying said adjusted function to subsequent spectral data measured on said second photoelectron spectroscopy system.

6. A metrology method applied to a sample film comprising:
obtaining a first set of spectral data measured for a first sample film measured by a first photoelectron spectroscopy system;
using a shape function to extract intensities for more than one elemental species associated with said first sample film to provide a first set of extracted intensities;
determining a first quantitative characteristic associated with said first sample film using at least one value from said first set of extracted intensities;
obtaining a second set of spectral data measured for a comparable sample film measured by a second photoelectron spectroscopy system, said comparable sample film being one of said first sample film or another film that can be compared to said first sample film;
continually adjusting said shape function and applying an adjusted shape function to extract intensities for said one or more elemental species associated with said comparable sample film to provide a second set of corrected-extracted intensities; and
determining a second quantitative characteristic for said comparable sample, said second quantitative characteristic being of same type to said first quantitative characteristic, and
wherein said shape function is continually adjusted until said determined second quantitative characteristic is in agreement with said first quantitative characteristic.

7. The method of claim 6 further comprising:
determining transmission correction factors for each intensity value which when applied to said second set of corrected-extracted intensities allows said second set of corrected-extracted intensities to be equal to said first set of extracted intensities.

8. The method of claim 6 further comprising:
applying said transmission correction factors to subsequent spectral data measured on said second photoelectron spectroscopy system.

9. The method of claim 6 further comprising:
applying said adjusted function to subsequent spectral data measured on said second photoelectron spectroscopy system.

10. The method of claim 6 further comprising:
determining adjusted shape functions over a broad spectrum range of intensities expected for a film.

11. The method of claim 10, wherein determining said adjusted shape functions over a broad spectrum range of intensities expected for a film further comprising:
obtaining a plurality of first set of spectral data measured for a plurality of first sample films measured by said first photoelectron spectroscopy system;
using shape functions to extract intensities for a plurality of elemental species associated with each of said plurality of first sample films to provide first extracted intensities;
determining said first quantitative characteristic associated with each of said plurality of first sample films using said first extracted intensities;
obtaining a plurality of second set of spectral data measured for a plurality of comparable sample films measured by said second photoelectron spectroscopy system, said comparable sample films being one of said first sample films or other films that can be compared to said first sample films;
continually adjusting said shape functions and applying adjusted shape functions to extract intensities for said plurality of elemental species associated with said comparable sample films to provide second corrected-extracted intensities; and
determining said second quantitative characteristic associated with each of said comparable sample films, said second quantitative characteristic being of same type to said first quantitative characteristic, and
wherein said shape functions are continually adjusted until said determined second quantitative characteristic determined for each said comparable sample films is in agreement with respective said first quantitative characteristic and wherein said adjusted shape functions over a broad spectrum range of intensities expected for a film are determined based on how said shape functions are adjusted to arrive to said agreement.

12. The method of claim 11 further comprising:
applying said transmission correction factors to subsequent spectral data measured on said second photoelectron spectroscopy system.

13. The method of claim 11 further comprising:
applying said adjusted functions to subsequent spectral data measured on said second photoelectron spectroscopy system.

14. The method of claim 13 further comprising:
determining an adjusted shape function using said adjusted shape functions determined for said second corrected-extracted intensities by any one of interpolation, extrapolation, or correlation.

15. The method of claim 14 further comprising:
determining an adjusted shape function using said adjusted shape functions obtained for said second corrected-extracted intensities by any one of interpolation, extrapolation, or correlation.

16. The method of claim 14 further comprising:
determining a transmission correction factor using said transmission correction factors obtained for said second corrected-extracted intensities by any one of interpolation, extrapolation, or correlation.

17. The method of claim 14 further comprising:
determining a transmission correction factor shape as a function of photoelectron energy using said quantitative characteristics formed by ratios of said second corrected-extracted intensities by any one of interpolation, extrapolation, or correlation, wherein an overall magnitude of transmission correction factor shape function with respect to the transmission function of said first photoelectron spectroscopy system does not need to be determined.

18. A system for characterizing a film while matching results from the system to a control system, wherein the system comprises:
an x-ray source operable to irradiate one or more films with x-rays resulting in an escape of photoelectrons;
an analyzer operable to detect escaping photoelectrons wherein the analyzer is operable to generate a signal representative of detected photoelectrons for use in providing an acquired spectrum for the film;
a computing apparatus operable to:
recognize a spectral peak shape of the acquired spectrum of at least one component of the film, wherein the film is formed on a substrate;
extract at least one intensity value associated with said acquired spectrum using a selected shape function with continually adjusting said selected shape function to extract said at least one intensity value, wherein said selected shape function is adjusted until that said extracted intensity value is in agreement with a control intensity value extracted from a control spectrum using said selected shape function measured from a control system;
store an adjusted shape function for said at least one intensity value, said adjusted shape function being obtained when said extracted intensity value is in agreement with said control intensity value; and
determine at least one quantitative measurement for said film.

19. The system of claim 18, wherein the computing apparatus is further operable to:
calculate a spectral background from said acquired spectrum; and
subtract said spectral background from said acquired spectrum.

20. The system of claim 18, wherein the computing apparatus is further operable to:
recognize overlapping peak areas and non-overlapping peak areas; and
using appropriate a shape function to extract an intensity value associated with a peak area.

21. The system of claim 18, wherein the computing apparatus is further operable to:
determine a transmission correction factor such that when applied to said extracted intensity value causes said extracted intensity value to be equal to said control intensity value; and
store said transmission correction factor.

22. The system of claim 18, wherein the computing apparatus is further operable to:
determine transmission correction factors over a broad spectrum of possible peak areas for a selected range of films;
store said transmission correction factors;
correlate said transmission correction factors to extracted intensity values; and
determine a second transmission correction factor for an extracted intensity for a sample film by interpolation or extrapolation.

23. The system of claim 18, wherein the computing apparatus is further operable to:
determine adjusted shape functions over a broad spectrum of possible peak areas for a selected range of films;
store said adjusted shape functions;
correlate said adjusted shape functions to respective peak areas; and
determine an adjusted shape function to be used for a sample peak area by interpolation or extrapolation.

24. A program storage media, readable by a media read apparatus under control of a computer, tangibly embodying a program executable to perform a process for characterizing a film while matching results from the system to a control system, wherein the program is operable to:
recognize a spectral peak shape of an acquired spectrum of at least one component of a film, wherein the film is formed on a substrate, and wherein said acquired spectrum contains a signal representative of detectable photoelectrons irradiated from the film by an x-ray source;
extract at least one intensity value associated with said acquired spectrum using a selected shape function with continually adjusting said selected shape function to extract said at least one intensity value, wherein said selected shape function is adjusted until that said extracted intensity value is in agreement with a control intensity value extracted from a control spectrum using said selected shape function measured from a control system;
store an adjusted shape function for said at least one intensity value, said adjusted shape function being obtained when said extracted intensity value is in agreement with said control intensity value; and
determine at least one quantitative measurement for said film.

25. The program storage media of claim 24, wherein the program is further operable to:
calculate a spectral background from said acquired spectrum; and
subtract said spectral background from said acquired spectrum.

26. The program storage media of claim 24, wherein the program is further operable to:
recognize overlapping peak areas and non-overlapping peak areas; and
using appropriate a shape function to extract an intensity value associated with a peak area.

27. The program storage media of claim 24, wherein the program is further operable to:
determine a transmission correction factor such that when applied to said extracted intensity value causes said extracted intensity value to be equal to said control intensity value; and
store said transmission correction factor.

28. The program storage media of claim 24, wherein the program is further operable to:
determine transmission correction factors over a broad spectrum of possible peak areas for a selected range of films;
store said transmission correction factors;
correlate said transmission correction factors to extracted intensity values;
determine a second transmission correction factor for an extracted intensity for a sample film by interpolation or extrapolation.

29. The program storage media of claim 24, wherein the program is further operable to:
determine adjusted shape functions over a broad spectrum of possible peak areas for a selected range of films;
store said adjusted shape functions;
correlate said adjusted shape functions to respective peak areas; and
determine an adjusted shape function to be used for a sample peak area by interpolation or extrapolation.

* * * * *